United States Patent
Van Gruijthuijsen et al.

(10) Patent No.: US 12,383,477 B2
(45) Date of Patent: Aug. 12, 2025

(54) COMPOSITE MICROCAPSULES

(71) Applicant: FIRMENICH SA, Satigny (CH)

(72) Inventors: Kitty Van Gruijthuijsen, Satigny (CH); Gregory Dardelle, Satigny (CH); Arnaud Struillou, Satigny (CH); Philipp Erni, Satigny (CH)

(73) Assignee: FIRMENICH SA, Satigny (CH)

( * ) Notice: Subject to any disclaimer, the term of this patent is extended or adjusted under 35 U.S.C. 154(b) by 745 days.

(21) Appl. No.: 17/439,353

(22) PCT Filed: Jul. 29, 2020

(86) PCT No.: PCT/EP2020/071369
§ 371 (c)(1),
(2) Date: Sep. 14, 2021

(87) PCT Pub. No.: WO2021/018947
PCT Pub. Date: Feb. 4, 2021

(65) Prior Publication Data
US 2022/0175635 A1    Jun. 9, 2022

(30) Foreign Application Priority Data

Jul. 30, 2019  (EP) .................................. 19189145

(51) Int. Cl.
| | | |
|---|---|---|
| *A61K 8/11* | (2006.01) | |
| *A61K 8/40* | (2006.01) | |
| *A61K 8/65* | (2006.01) | |
| *A61K 8/73* | (2006.01) | |
| *A61Q 5/02* | (2006.01) | |
| *A61Q 5/12* | (2006.01) | |
| *A61Q 13/00* | (2006.01) | |
| *A61Q 19/10* | (2006.01) | |
| *B01J 13/16* | (2006.01) | |
| *C11D 1/14* | (2006.01) | |
| *C11D 1/22* | (2006.01) | |
| *C11D 1/72* | (2006.01) | |
| *C11D 1/83* | (2006.01) | |
| *C11D 3/00* | (2006.01) | |
| *C11D 3/50* | (2006.01) | |
| *C11D 17/00* | (2006.01) | |

(52) U.S. Cl.
CPC .................. *A61K 8/11* (2013.01); *A61K 8/40* (2013.01); *A61K 8/65* (2013.01); *A61K 8/73* (2013.01); *A61K 8/736* (2013.01); *A61Q 5/02* (2013.01); *A61Q 5/12* (2013.01); *A61Q 13/00* (2013.01); *A61Q 19/10* (2013.01); *B01J 13/16* (2013.01); *C11D 1/83* (2013.01); *C11D 3/0015* (2013.01); *C11D 3/505* (2013.01); *C11D 17/0013* (2013.01); *C11D 17/0039* (2013.01); *A61K 2800/412* (2013.01); *C11D 1/143* (2013.01); *C11D 1/22* (2013.01); *C11D 1/721* (2013.01); *C11D 2111/12* (2024.01)

(58) Field of Classification Search
None
See application file for complete search history.

(56) References Cited

U.S. PATENT DOCUMENTS

| | | | |
|---|---|---|---|
| 3,897,361 | A | 7/1975 | Saeki et al. |
| 6,309,426 | B1 | 10/2001 | Dias et al. |
| 10,034,819 | B2 * | 7/2018 | Dardelle .................. A61K 8/87 |
| 11,179,302 | B2 * | 11/2021 | Dardelle .................. B01J 13/14 |
| 2011/0077188 | A1 | 3/2011 | Ouali et al. |
| 2011/0152146 | A1 | 6/2011 | Denutte et al. |
| 2013/0230574 | A1 | 9/2013 | Struillou et al. |
| 2015/0250689 | A1 | 9/2015 | Dardelle et al. |

FOREIGN PATENT DOCUMENTS

| | | |
|---|---|---|
| GB | 1257178 A | 12/1971 |
| WO | 2007004166 A1 | 1/2007 |
| WO | 2013068255 A1 | 5/2013 |
| WO | 2017134179 A1 | 8/2017 |
| WO | 2018002214 A1 | 1/2018 |
| WO | 2018115250 A1 | 6/2018 |
| WO | 2019077052 A1 | 4/2019 |
| WO | 2019243425 A1 | 12/2019 |
| WO | 2019243427 A1 | 12/2019 |
| WO | 2020127743 A1 | 6/2020 |
| WO | 2020127749 A1 | 6/2020 |
| WO | 2020131855 A1 | 6/2020 |

(Continued)

OTHER PUBLICATIONS

Detergents—Detergents The main surfactants used in detergents and personal care products Louis Ho Tan Tai and Véronique Nardello-Rataj OCL, 8 2 (2001) 141-144 DOI: https://doi.org/10.1051/ocl.2001.0141 (Year: 2001).*

Puchta, R. Cationic surfactants in laundry detergents and laundry aftertreatment aids. J Am Oil Chem Soc 61, 367-376 (1984). https://doi.org/10.1007/BF02678796 (Year: 1984).*

Yelloji-Rao K. Mirajkar. Applications of Surfactants in Shampoos. Handbook of Detergents, Part E 1st Edition, 151-181 (2008) (Year: 2008).*

(Continued)

*Primary Examiner* — Johann R Richter
*Assistant Examiner* — Afua Bamfoaa Boateng
(74) *Attorney, Agent, or Firm* — Armstrong Teasdale LLP

(57) ABSTRACT

Described herein is a composite microcapsule slurry including at least one microcapsule having an oil-based core including a hydrophobic material, preferably a perfume, and a composite shell including a first material and a second material. The first material and the second material are different, the first material is a coacervate, the second material is a polymeric material, and the weight ratio in the slurry between the first material and the second material is between 50:50 and 99.9:0.1.

17 Claims, 4 Drawing Sheets

(56) References Cited

FOREIGN PATENT DOCUMENTS

WO      2020131875 A2    6/2020
WO      2020209907 A1    10/2020

OTHER PUBLICATIONS

International Search Report and Written Opinion for International Patent Application No. PCT/EP2020/071369, mailed Sep. 25, 2020, 14 pages.
Parker et al. "Glassy dynamics of gelatin gels." Soft Matter, 2010, 6, 4916-4919.

* cited by examiner

COMPOSITE MICROCAPSULES

CROSS-REFERENCE TO RELATED APPLICATIONS

This application is a U.S. National Phase Application of International Patent Application No. PCT/EP2020/071369, filed Jul. 29, 2020, which claims the benefit of priority to European Patent Application No. 19189145.6, filed Jul. 30, 2019, each of which are hereby incorporated by reference herein.

FIELD OF THE INVENTION

The invention relates to microcapsules comprising both a core and a composite shell formed by a coacervate and a polymeric material. Consumer products comprising those microcapsules are also objects of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing active ingredients, for example a perfume, are needed to protect and later release the core payload when triggered. A key requirement from the industry regarding these systems is to survive suspension in challenging bases without physically dissociating or degrading. This is referred to as chemical stability for the delivery system. For instance, fragranced personal and household cleansers containing high levels of aggressive surfactant detergents are very challenging for the stability of microcapsules. High levels of surfactants also increase the speed of diffusion of actives out of the microcapsules. This leads to leakage of the actives during storage and a reduced impact when the microcapsules are triggered to release. In addition, the mechanical stability of microcapsules can be compromised by physical forces, such as crushing, or other methods that compromise the integrity of the microcapsules.

Even if microcapsules are known from the prior art, there is still a need in the industry for new microcapsules with improved barrier and release properties for encapsulated materials. The present invention satisfies this and other needs of the industry.

SUMMARY OF THE INVENTION

It has now been found that performing microcapsules encapsulating a hydrophobic material such as perfume oil could be obtained by forming a composite wall formed from a first coacervate material and a second polymeric material according to a specific weight ratio. Unexpectedly, it has been shown that those capsules demonstrate a good balance between a high performance in terms of chemical stability and high performance in terms of mechanical stability.

In a first aspect, the present invention relates to a composite microcapsule slurry comprising at least one microcapsule having:
  an oil-based core comprising an hydrophobic material, preferably a perfume
  a composite shell comprising a first material and a second material, wherein:
    the first material and the second material are different,
    the first material is a coacervate,
    the second material is a polymeric material, and
    the weight ratio in the slurry between the first material and the second material is comprised between 50:50 and 99.9:0.1.

In other aspects, the present invention relates to a consumer product in the form of a shampoo, a shower gel, a rinse-off conditioning composition, a hair-coloration, a liquid detergent or a fabric softener comprising the microcapsule slurry as defined above.

DETAILED DESCRIPTION OF THE INVENTION

Unless stated otherwise, percentages (%) are meant to designate a percentage by weight of a composition.

By "hydrophobic material", it is meant any hydrophobic material—single material or a mixture of materials—which forms a two-phase dispersion when mixed with water.

By "ingredient", it is meant a single compound or a combination of ingredients.

By "perfume or flavour oil", it is meant a single perfuming or flavouring compound or a mixture of several perfuming or flavouring compounds.

By "consumer product" or "end-product" it is meant a manufactured product ready to be distributed, sold and used by a consumer.

According to the invention, the wordings "acyl chloride", "poly acyl chloride", "acid chloride" and "poly acid chloride" are used indifferently.

A "microcapsule", or the similar, in the present invention it is meant that core-shell microcapsules have a particle size distribution in the micron range (e.g. a mean diameter(Dv (50) comprised between about 1 and 3000 microns) and comprise an external polymer-based shell and an internal continuous oil phase enclosed by the external shell. According to an embodiment, microcapsules have a mean diameter comprised between 1 and 500 microns, preferably from 2 and 200, more preferably between 4 and 100 microns.

According to the invention, the wordings "mean diameter" or "mean size" are used indifferently. According to an embodiment, microcapsules are not agglomerated. According to another embodiment, microcapsules are partly agglomerated. Still according to another embodiment, the totality of the microcapsules is agglomerated.

By "microcapsule slurry", it is meant microcapsule(s) that is (are) dispersed in a liquid. According to an embodiment, the slurry is an aqueous slurry, i.e the microcapsule(s) is (are) dispersed in an aqueous phase.

By "composite microcapsule slurry", it is meant a core-shell microcapsule slurry having a composite shell, namely a shell comprising at least two different materials (a first coacervate material and a second polymeric material). According to the invention, "coacervate" or "hydrogel" can be used indifferently. By hydrogel, it is meant a polymer network swollen with water.

The coacervate can be a "simple" coacervate (i.e made by "simple" coacervation) or a complex coacervate (i.e made by "complex" coacervation). By simple coacervation, it is understood that one polyelectrolyte alone made to undergo phase separation and is then used to form the coacervate material of the shell. By complex coacervation are understood methods in which at least two polyelectrolytes together form the coacervate material of the shell.

According to a particular embodiment, the coacervate is a complex coacervate. In other words, according to this embodiment, the complex coacervate comprises at least a first polyelectrolyte and a second polyelectrolyte.

According to a particular embodiment, the microcapsule shell has an inner layer formed of the second material and an outer layer formed of the coacervate. According to an embodiment, the inner and the outer layers are interlinked layers, it is meant a shell consisting of layers that are linked by chemical or physical interactions, thereby forming one composite structure. As physical or chemical interactions, one may cite covalent bonds, ionic bonds, coordinate covalent bonds, hydrogen bonds, van der Waals interaction, hydrophobic interactions, chelation, or steric effects.

The present invention provides core-shell microcapsules having a composite shell comprising a first coacervate material and a second polymeric material, preferably having a hydrogel/polyurea composite structure. Such membrane compositions and particular structure have been designed and have shown to provide benefits such as chemical stability and mechanical stability.

Two processes are combined in the present invention, namely, the coacervation, preferably complex coacervation process and an interfacial polymerization process to obtain microcapsules having good properties.

Although the complex coacervation process and the interfacial polymerization process are each known in the art, the present invention provides new microcapsules having a specific ratio between the first and the second material. It has been shown that even with a reduced amount of the second material (polymeric material), the microcapsules are still stable in challenging media.

Figures Brief Description of the Drawings

MICROCAPSULE SLURRY

Figure 1:
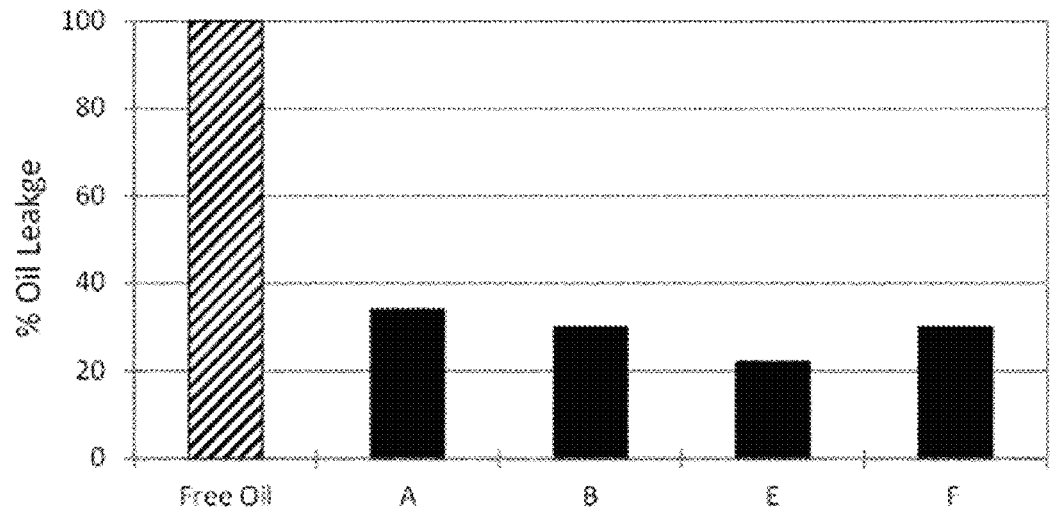
FIG. 1 and FIG. 2 represent oil leakage of microcapsules according to the invention in a fabric softener.

A first object of the invention is therefore a composite microcapsule slurry comprising at least one microcapsule having:
 an oil-based core comprising a hydrophobic material, preferably a perfume
 a composite shell comprising a first material and a second material, wherein:
  the first material and the second material are different,
  the first material is a coacervate,
  the second material is a polymeric material, and
  the weight ratio in the slurry between the first material and the second material is comprised between 50:50 and 99.9:0.1.

According to an embodiment, the weight ratio in the slurry between the first material and the second material is comprised between 80:20 and 99.9:0.1.

Hydrophobic Material

According to an embodiment, the hydrophobic material is a hydrophobic active ingredient.

According to a preferred embodiment, the active ingredient comprises a perfume oil or a flavour oil. Alternative ingredients which could benefit from being encapsulated could be used either instead of a perfume or flavour, or in combination with a perfume or flavour. Non-limiting examples of such ingredients include a cosmetic, skin caring, malodour counteracting, bactericide, fungicide, pharmaceutical or agrochemical ingredient, a sanitizing agent, an insect repellent or attractant, and mixture thereof.

The nature and type of the insect repellent or attractant that can be present in the hydrophobic internal phase do not warrant a more detailed description here, which in any case would not be exhaustive, the skilled person being able to select them on the basis of its general knowledge and according to the intended use or application.

Examples of such insect repellent or attractant are birch, DEET (N,N-diethyl-m-toluamide), essential oil of the lemon eucalyptus (*Corymbia citriodora*) and its active compound p-menthane-3,8-diol (PMD), icaridin (hydroxyethyl isobutyl piperidine carboxylate), Nepelactone, Citronella oil, Neem oil, Bog Myrtle (*Myrica* Gale), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

By "perfume oil" (or also "perfume") or "flavour" what is meant here is an ingredient or composition that is a liquid at about 20° C. Said perfume or flavour oil can be a perfuming or flavouring ingredient alone or a mixture of ingredients in the form of a perfuming or flavouring composition. As a "perfuming ingredient" it is meant here a compound, which is used in perfuming preparations or compositions to impart as primary purpose a hedonic effect. In other words such an ingredient, to be considered as being a perfuming one, must be recognized by a person skilled in the art as being able to at least impart or modify in a positive or pleasant way the odor of a composition, and not just as having an odor. The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said ingredients may also be compounds known to release in a controlled manner various types of perfuming compounds.

In particular one may cite perfuming ingredients which are commonly used in perfume formulations, such as:
 Aldehydic ingredients: decanal, dodecanal, 2-methyl-undecanal, 10-undecenal, octanal, nonanal and/or nonenal;
 Aromatic-herbal ingredients: eucalyptus oil, camphor, eucalyptol, 5-methyltricyclo[6.2.1.0~2,7~]undecan-4-one, 1-methoxy-3-hexanethiol, 2-ethyl-4,4-dimethyl-1, 3-oxathiane, 2,2,7/8,9/10-Tetramethylspiro[5.5]undec-8-en-1-one, menthol and/or alpha-pinene;
 Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecane-dione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1S)-1-[(1R)-3,3-dimethylcyclohexyl]ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-oneand/or (1S,1'R)-[1-(3',3'-dimethyl-1'-cyclohexyl)ethoxycarbonyl]methyl propanoate;

Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

It is also understood that said co-ingredients may also be compounds known to release in a controlled manner various types of perfuming compounds also known as properfume or profragrance. Non-limiting examples of suitable properfume may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-phenylethyl oxo(phenyl)acetate, 3,7-dimethyl-2,6-octadien-1-yl hexadecanoate, (2-((2-methylundec-1-en-1-yl)oxy)ethyl)benzene, 1-methoxy-4-(3-methyl-4-phenethoxybut-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en-2-yl)benzene, 2-(1-phenethoxyprop-1-en-2-yl)naphthalene, (2-phenethoxyvinyl)benzene, 2-(1-((3,7-dimethyloct-6-en-1-yl)oxy)prop-1-en-2-yl) naphthalene or a mixture thereof.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to an embodiment, the perfuming ingredients have a high steric hindrance and are in particular those from one of the following groups:

Group 1: perfuming ingredients comprising a cyclohexane, cyclohexene, cyclohexanone or cyclohexenone ring substituted with at least one linear or branched $C_1$ to $C_4$ alkyl or alkenyl substituent;

Group 2: perfuming ingredients comprising a cyclopentane, cyclopentene, cyclopentanone or cyclopentenone ring substituted with at least one linear or branched $C_4$ to $C_8$ alkyl or alkenyl substituent;

Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;

Group 4: perfuming ingredients comprising at least two fused or linked $C_5$ and/or $C_6$ rings;

Group 5: perfuming ingredients comprising a camphor-like ring structure;

Group 6: perfuming ingredients comprising at least one C7 to C20 ring structure;

Group 7: perfuming ingredients having a log P value above 3.5 and comprising at least one tert-butyl or at least one trichloromethyl substitutent;

Examples of ingredients from each of these groups are:

Group 1: 2,4-dimethyl-3-cyclohexene-1-carbaldehyde (origin: Firmenich SA, Geneva, Switzerland), isocyclocitral, menthone, isomenthone, methyl 2,2-diethyl-6-methylene-1-cyclohexanecarboxylate (origin: Firmenich SA, Geneva, Switzerland), nerone, terpineol, dihydroterpineol, terpenyl acetate, dihydroterpenyl acetate, dipentene, eucalyptol, hexylate, rose oxide, (S)-1,8-p-menthadiene-7-ol (origin: Firmenich SA, Geneva, Switzerland), 1-p-menthene-4-ol, (1RS,3RS,4SR)-3-p-mentanyl acetate, (1R,2S,4R)-4,6,6-trimethyl-bicyclo[3,1,1]heptan-2-ol, tetrahydro-4-methyl-2-phenyl-2H-pyran (origin: Firmenich SA, Geneva, Switzerland), cyclohexyl acetate, cyclanol acetate, 1,4-cyclohexane diethyldicarboxylate (origin: Firmenich SA, Geneva, Switzerland), (3ARS,6SR,7ASR)-perhydro-3,6-dimethyl-benzo[B]furan-2-one (origin: Firmenich SA, Geneva, Switzerland), ((6R)-perhydro-3,6-dimethyl-benzo[B]furan-2-one (origin: Firmenich SA, Geneva, Switzerland), 2,4,6-trimethyl-4-phenyl-1,3-dioxane, 2,4,6-trimethyl-3-cyclohexene-1-carbaldehyde;

Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3'-cyclopenten-1'-yl)-2-buten-1-ol (origin: Firmenich SA, Geneva, Switzerland), (1'R,E)-3,3-dimethyl-5-(2',2',3'-trimethyl-3'-cyclopenten-1'-yl)-4-penten-2-ol (origin: Firmenich SA, Geneva, Switzerland), 2-heptylcyclopentanone, methyl-cis-3-oxo-2-pentyl-1-cyclopentane acetate (origin: Firmenich SA, Geneva, Switzerland), 2,2,5-Trimethyl-5-pentyl-1-cyclopentanone (origin: Firmenich SA, Geneva, Switzerland), 3,3-dimethyl-5-(2,2,3-trimethyl-3-cyclopenten-1-yl)-4-penten-2-ol (origin: Firmenich SA, Geneva, Switzerland), 3-methyl-5-(2,2,3-trimethyl-3-cyclopenten-1-yl)-2-pentanol (origin, Givaudan SA, Vernier, Switzerland);

Group 3: damascones, 1-(5,5-dimethyl-1-cyclohexen-1-yl)-4-penten-1-one (origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, mixture of 1-(5,5-dimethyl-1-cyclohexen-1-yl)-4-penten-1-one and 1-(3,3-dimethyl-1-cyclohexen-1-yl)-4-penten-1-one (origin: Firmenich SA, Geneva, Switzerland), 1-(2,6,6-trimethyl-1-cyclohexen-1-yl)-2-buten-1-one (origin: Firmenich SA, Geneva, Switzerland), (1S,1'R)-[1-(3',3'-Dimethyl-1'-cyclohexyl)ethoxycarbonyl]methyl propanoate (origin: Firmenich SA, Geneva, Switzerland), 2-tert-butyl-1-cyclohexyl acetate (origin: International Flavors and Fragrances, USA), 1-(2,2,3,6-tetramethyl-cyclohexyl)-3-hexanol (origin: Firmenich SA, Geneva, Switzerland), trans-1-(2,2,6-trimethyl-1-cyclohexyl)-3-hexanol (origin: Firmenich SA, Geneva, Switzerland), (E)-3-methyl-4-(2,6,6-trimethyl-2-cyclohexen-1-yl)-3-buten-2-one, terpenyl isobutyrate, 4-(1,1-dimethylethyl)-1-cyclohexyl acetate (origin: Firmenich SA, Geneva, Switzerland), 8-methoxy-1-p-menthene, (1S,1'R)-2-[1-(3',3'-dimethyl-1'-cyclohexyl)ethoxy]-2-methylpropyl propanoate (origin: Firmenich SA, Geneva, Switzerland), para tert-butylcyclohexanone, menthenethiol, 1-methyl-4-(4-methyl-3-pentenyl)-3-cyclohexene-1-carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), a mixture of (1RS,2SR,6RS,7RS,8SR)-tricyclo[5.2.1.0~2,6~]dec-3-en-8-yl 2-methylpropanoate and (1RS,2SR,6RS,7RS,8SR)-tricyclo[5.2.1.0~2,6~]dec-4-en-8-yl 2-methylpropanoate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR,10RS) isomer, 6-ethyl-2,10,10-trimethyl-1-oxaspiro[4.5]deca-3,6-diene, 1,2,3,5,6,7-hexahydro-1,1,2,3,3-pentamethyl-4-indenone (origin: International Flavors and Fragrances, USA), a mixture of 3-(3,3-dimethyl-5-indanyl)propanal and 3-(1,1-dimethyl-5-indanyl)propanal (origin: Firmenich SA, Geneva, Switzerland), 3',4-dimethyl-tricyclo[6.2.1.0(2,7)]undec-4-ene-9-spiro-2'-oxirane (origin: Firmenich SA, Geneva, Switzerland), 9/10-ethyldiene-3-oxatricyclo[6.2.1.0(2,7)]undecane, (perhydro-5,5,8A-trimethyl-2-naphthalenyl acetate (origin: Firmenich SA, Geneva, Switzerland), octalynol, (dodecahydro-3a,6,6,9a-tetramethyl-naphtho[2,1-b]furan, origin: Firmenich SA, Geneva, Switzerland), tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, pinene, camphene, 8-methoxycedrane, (8-methoxy-2,6,6,8-tetramethyl-tricyclo[5.3.1.0(1,5)]undecane (origin: Firmenich SA, Geneva, Switzerland), cedrene, cedrenol, cedrol, mixture of 9-ethylidene-3-oxatricyclo[6.2.1.0(2,7)]undecan-4-one and 10-ethylidene-3-oxatricyclo[6.2.1.0(2,7)]undecan-4-one (origin: Firmenich SA, Geneva, Switzerland), 3-methoxy-7,7-dimethyl-10-methylene-bicyclo[4.3.1]decane (origin: Firmenich SA, Geneva, Switzerland);

Group 6: (trimethyl-13-oxabicyclo-[10.1.0]-trideca-4,8-diene (origin: Firmenich SA, Geneva, Switzerland), Ambrettolide LG ((E)-9-hexadecen-16-olide, origin: Firmenich SA, Geneva, Switzerland), pentadecenolide (origin: Firmenich SA, Geneva, Switzerland), muscenone (3-methyl-(4/5)-cyclopentadecenone, origin: Firmenich SA, Geneva, Switzerland), 3-methylcyclopentadecanone (origin: Firmenich SA, Geneva, Switzerland), pentadecanolide (origin: Firmenich SA, Geneva, Switzerland), cyclopentadecanone (origin:

Firmenich SA, Geneva, Switzerland), 1-ethoxyethoxy) cyclododecane (origin: Firmenich SA, Geneva, Switzerland), 1,4-dioxacycloheptadecane-5,17-dione, 4,8-cyclododecadien-1-one;

Group 7: (+−)-2-methyl-3-[4-(2-methyl-2-propanyl)phenyl]propanal (origin: Givaudan SA, Vernier, Switzerland), 2,2,2-trichloro-1-phenylethyl acetate.

The perfume can comprise at least 30%, particularly at least 50%, more particularly at least 60% of ingredients selected from Groups 1 to 7, as defined above. According to an embodiment, said perfume comprises at least 30%, particularly at least 50% of ingredients from Groups 3 to 7, as defined above. According to an embodiment, said perfume comprises at least 30%, preferably at least 50% of ingredients from Groups 3, 4, 6 or 7, as defined above.

According to another particular embodiment, the perfume comprises at least 30%, preferably at least 50%, more preferably at least 60% of ingredients having a log P above 3, preferably above 3.5 and even more preferably above 3.75.

According to an embodiment, the perfume used in the invention contains less than 10% of its own weight of primary alcohols, less than 15% of its own weight of secondary alcohols and less than 20% of its own weight of tertiary alcohols. Advantageously, the perfume used in the invention does not contain any primary alcohols and contains less than 15% of secondary and tertiary alcohols.

According to an embodiment, the oil phase (or the oil-based core) comprises:

25-100 wt % of a perfume oil comprising at least 15 wt % of high impact perfume raw materials having a Log T<−4, and 0-75 wt % of a density balancing material having a density greater than 1.07 g/cm$^3$.

"High impact perfume raw materials" should be understood as perfume raw materials having a Log T<−4. The odor threshold concentration of a chemical compound is determined in part by its shape, polarity, partial charges and molecular mass. For convenience, the threshold concentration is presented as the common logarithm of the threshold concentration, i.e., Log [Threshold] ("Log T").

A "density balancing material" should be understood as a material having a density greater than 1.07 g/cm$^3$ and having preferably low or no odor.

The odor threshold concentration of a perfuming compound is determined by using a gas chromatograph ("GC"). Specifically, the gas chromatograph is calibrated to determine the exact volume of the perfume oil ingredient injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and hence the concentration of the perfuming compound. To determine the threshold concentration, solutions are delivered to the sniff port at the back-calculated concentration. A panelist sniffs the GC effluent and identifies the retention time when odor is noticed. The average across all panelists determines the odor threshold concentration of the perfuming compound. The determination of odor threshold is described in more detail in C. Vuilleumier et al., Multi-dimensional Visualization of Physical and Perceptual Data Leading to a Creative Approach in Fragrance Development, Perfume & Flavorist, Vol. 33, September, 2008, pages 54-61. The nature of high impact perfume raw materials having a Log T<−4 and density balancing material having a density greater than 1.07 g/cm$^3$ are described in WO2018115250, the content of which are included by reference.

According to an embodiment, the high impact perfume raw materials having a Log T<−4 are selected from the list in Table A below.

Table A: high impact perfume raw materials having a Log T<−4

TABLE A high impact perfume raw materials having a Log T<−4
Perfume raw materials (Log T<−4)

(+−)-1-METHOXY-3-HEXANETHIOL
4-(4-HYDROXY-1-PHENYL)-2-BUTANONE
(+−)-2-(4-METHYL-3-CYCLOHEXEN-1-YL)-2-PROPANETHIOL
2-METHOXY-4-(1-PROPENYL)-1-PHENYL ACETATE
PYRAZOBUTYLE
3-PROPYLPHENOL
1-(3-METHYL-1-BENZOFURAN-2-YL)ETHANONE
2-(3-PHENYLPROPYL)PYRIDINE
1-(3,3-DIMETHYL-1-CYCLOHEXEN-1-YL)-4-PENTEN-1-ONE (A) +
1-(5,5-DIMETHYL-1-CYCLOHEXEN-1-YL)-4-PENTEN-1-ONE (B)
1-(5,5-DIMETHYL-1-CYCLOHEXEN-1-YL)-4-PENTEN-1-ONE
(3RS,3ARS,6SR,7ASR)-PERHYDRO-3,6-DIMETHYL-BENZO[B]FURAN-2-ONE (A) + (3SR,3ARS,6SR,7ASR)-PERHYDRO-3,6-DIMETHYL-BENZO[B]FURAN-2-ONE (B)
(+−)-1-(5-ETHYL-5-METHYL-1-CYCLOHEXEN-1-YL)-4-PENTEN-1-ONE
(1'S,3'R)-1-METHYL-2-[(1',2',2'-TRIMETHYLBICYCLO[3.1.0]HEX-3'-YL)METHYL]CYCLOPROPYL}METHANOL
(+−)-3-MERCAPTOHEXYL ACETATE
(2E)-1-(2,6,6-TRIMETHYL-1,3-CYCLOHEXADIEN-1-YL)-2-BUTEN-1-ONE
7-METHYL-2H-1,5-BENZODIOXEPIN-3(4H)-ONE
(2E,6Z)-2,6-NONADIEN-1-OL
(4Z)-4-DODECENAL
(+−)-4-HYDROXY-2,5-DIMETHYL-3(2H)-FURANONE
METHYL 2,4-DIHYDROXY-3,6-DIMETHYLBENZOATE
3-METHYLINDOLE
(+−)-PERHYDRO-4ALPHA,8ABETA-DIMETHYL-4A-NAPHTHALENOL
PATCHOULOL
2-METHOXY-4-(1-PROPENYL)PHENOL
(+−)-5,6-DIHYDRO-4-METHYL-2-PHENYL-2H-PYRAN (A) + TETRAHYDRO-4-METHYLENE-2-PHENYL-2H-PYRAN (B)
4-METHYLENE-2-PHENYLTETRAHYDRO-2H-PYRAN (A) + (+−)-4-METHYL-2-PHENYL-3,6-DIHYDRO-2H-PYRAN (B)
4-HYDROXY-3-METHOXYBENZALDEHYDE
NONYLENIC ALDEHYDE
2-METHOXY-4-PROPYLPHENOL
(2Z)-3-METHYL-5-PHENYL-2-PENTENENITRILE (A) + (2E)-3-METHYL-5-PHENYL-2-PENTENENITRILE (B)
1-(SPIRO[4.5]DEC-6-EN-7-YL)-4-PENTEN-1-ONE (A) + 1-(SPIRO[4.5]DEC-7-EN-7-YL)-4-PENTEN-1-ONE (B)
2-METHOXYNAPHTHALENE
(−)-(3AR,5AS,9AS,9BR)-3A,6,6,9A-TETRAMETHYLDODECAHYDRONAPHTHO[2,1-B]FURAN
5-NONANOLIDE
(3AR,5AS,9AS,9BR)-3A,6,6,9A-TETRAMETHYLDODECAHYDRONAPHTHO[2,1-B]FURAN
7-ISOPROPYL-2H,4H-1,5-BENZODIOXEPIN-3-ONE
COUMARIN
4-METHYLPHENYL ISOBUTYRATE
(2E)-1-(2,6,6-TRIMETHYL-1,3-CYCLOHEXADIEN-1-YL)-2-BUTEN-1-ONE
BETA,2,2,3-TETRAMETHYL-DELTA-METHYLENE-3-CYCLOPENTENE-1-BUTANOL
DELTA DAMASCONE ((2E)-1-[(1RS,2SR)-2,6,6-TRIMETHYL-3-CYCLOHEXEN-1-YL]-2-BUTEN-1-ONE)
(+−)-3,6-DIHYDRO-4,6-DIMETHYL-2-PHENYL-2H-PYRAN
ANISALDEHYDE
PARACRESOL
3-ETHOXY-4-HYDROXYBENZALDEHYDE
METHYL 2-AMINOBENZOATE
ETHYL METHYLPHENYLGLYCIDATE
OCTALACTONE G
ETHYL 3-PHENYL-2-PROPENOATE

TABLE A-continued high impact perfume raw materials having a Log T<−4
Perfume raw materials (Log T<−4)

(−)-(2E)-2-ETHYL-4-[(1R)-2,2,3-TRIMETHYL-3-CYCLOPENTEN-1-YL]-2-BUTEN-1-OL
PARACRESYL ACETATE
DODECALACTONE
TRICYCLONE
(+)-(3R,5Z)-3-METHYL-5-CYCLOPENTADECEN-1-ONE
UNDECALACTONE
(1R,4R)-8-MERCAPTO-3-P-MENTHANONE
(3S,3AS,6R,7AR)-3,6-DIMETHYLHEXAHYDRO-1-BENZOFURAN-2(3H)-ONE
BETA IONONE
(+−)-6-PENTYLTETRAHYDRO-2H-PYRAN-2-ONE
(3E,5Z)-1,3,5-UNDECATRIENE
10-UNDECENAL (A) + (9E)-9-UNDECENAL (B) + (9Z)-9-UNDECENAL (C)
(Z)-4-DECENAL
(+−)-ETHYL 2-METHYLPENTANOATE
1,2-DIALLYLDISULFANE
(2Z)-2-TRIDECENENITRILE (A) + (3Z)-3-TRIDECENENITRILE (B) + (3E)-3-TRIDECENENITRILE (C) + (2E)-2-TRIDECENENITRILE (D)
(+−)-2-ETHYL-4,4-DIMETHYL-1,3-OXATHIANE
(+)-(3R,5Z)-3-METHYL-5-CYCLOPENTADECEN-1-ONE
3-(4-TERT-BUTYLPHENYL)PROPANAL
ALLYL (CYCLOHEXYLOXY)ACETATE
METHYLNAPHTHYLKETONE
(+−)-(4E)-3-METHYL-4-CYCLOPENTADECEN-1-ONE (A) + (+−)-(5E)-3-METHYL-5-CYCLOPENTADECEN-1-ONE (B) + (+−)-(5Z)-3-METHYL-5-CYCLOPENTADECEN-1-ONE (C)
CYCLOPROPYLMETHYL (3Z)-3-HEXENOATE (A) + CYCLOPROPYLMETHYL (3E)-3-HEXENOATE (B)
(4E)-4-METHYL-5-(4-METHYLPHENYL)-4-PENTENAL
(+−)-1-(5-PROPYL-1,3-BENZODIOXOL-2-YL)ETHANONE
4-METHYL-2-PENTYLPYRIDINE
(+−)-(E)-3-METHYL-4-(2,6,6-TRIMETHYL-2-CYCLOHEXEN-1-YL)-3-BUTEN-2-ONE
(3ARS,5ASR,9ASR,9BRS)-3A,6,6,9A-TETRAMETHYLDODECAHYDRONAPHTHO[2,1-B]FURAN
(2S,5R)-5-METHYL-2-(2-PROPANYL)CYCLOHEXANONE OXIME
6-HEXYLTETRAHYDRO-2H-PYRAN-2-ONE
(+−)-3-(3-ISOPROPYL-1-PHENYL)BUTANAL
METHYL 2-((1RS,2RS)-3-OXO-2-PENTYLCYCLOPENTYL)ACETATE (A) + METHYL 2-((1RS,2SR)-3-OXO-2-PENTYLCYCLOPENTYL)ACETATE (B)
1-(2,6,6-trimethyl-1-cyclohex-2-enyl)pent-1-en-3-one
INDOL
7-PROPYL-2H,4H-1,5-BENZODIOXEPIN-3-ONE
ETHYL PRALINE
(4-METHYLPHENOXY)ACETALDEHYDE
ETHYL TRICYCLO[5.2.1.0.(2,6)]DECANE-2-CARBOXYLATE
(+)-(1'S,2S,E)-3,3-DIMETHYL-5-(2',2',3'-TRIMETHYL-3'-CYCLOPENTEN-1'-YL)-4-PENTEN-2-OL
(2R,4E)-3,3-DIMETHYL-5-[(1R)-2,2,3-TRIMETHYL-3-CYCLOPENTEN-1-YL]-4-PENTEN-2-OL (A) + (2S,4E)-3,3-DIMETHYL-5-[(1R)-2,2,3-TRIMETHYL-3-CYCLOPENTEN-1-YL]-4-PENTEN-2-OL (B)
8-ISOPROPYL-6-METHYL-BICYCLO[2.2.2]OCT-5-ENE-2-CARBALDEHYDE
METHYLNONYLACETALDEHYDE
4-FORMYL-2-METHOXYPHENYL 2-METHYLPROPANOATE
(E)-4-DECENAL
(+−)-2-ETHYL-4-(2,2,3-TRIMETHYL-3-CYCLOPENTEN-1-YL)-2-BUTEN-1-OL
(1R,5R)-4,7,7-TRIMETHYL-6-THIABICYCLO[3.2.1]OCT-3-ENE (A) + (1R,4R,5R)-4,7,7-TRIMETHYL-6-THIABICYCLO[3.2.1]OCTANE (B)
(−)-(3R)-3,7-DIMETHYL-1,6-OCTADIEN-3-OL
(E)-3-PHENYL-2-PROPENENITRILE
4-METHOXYBENZYL ACETATE
(E)-3-METHYL-5-(2,2,3-TRIMETHYL-3-CYCLOPENTEN-1-YL)-4-PENTEN-2-OL
ALLYL (3-METHYLBUTOXY)ACETATE (A) + (+−)-ALLYL (2-METHYLBUTOXY)ACETATE
(+−)-(2E)-1-(2,6,6-TRIMETHYL-2-CYCLOHEXEN-1-YL)-2-BUTEN-1-ONE
(1E)-1-(2,6,6-TRIMETHYL-1-CYCLOHEXEN-1-YL)-1-PENTEN-3-ONE According to an embodiment, perfume raw materials having a Log T4 are chosen in the group consisting of aldehydes, ketones, alcohols, phenols, esters lactones, ethers, epoxydes, nitriles and mixtures thereof.

According to an embodiment, perfume raw materials having a Log T<−4 comprise at least one compound chosen in the group consisting of alcohols, phenols, esters lactones, ethers, epoxydes, nitriles and mixtures thereof, preferably in amount comprised between 20 and 7000 by weight based on the total weight of the perfume raw materials having a Log T<−4.

According to an embodiment, perfume raw materials having a Log T<−4 comprise between 20 and 70% by weight of aldehydes, ketones, and mixtures thereof based on the total weight of the perfume raw materials having a Log T<−4.

The remaining perfume raw materials contained in the oil-based core may have therefore a Log T>−4.

Non limiting examples of perfume raw materials having a Log T>−4 are listed in table B below.

TABLE B perfume raw materials having a Log T>−4
Perfume raw materials (Log T>−4)

ETHYL 2-METHYLBUTYRATE
(E)-3-PHENYL-2-PROPENYL ACETATE
(+−)-8-SEC-BUTYLQUINOLINE (A) + (+−)-6-SEC-BUTYLQUINOLINE
(+−)-3-(1,3-BENZODIOXOL-5-YL)-2-METHYLPROPANAL
VERDYLE PROPIONATE
1-(OCTAHYDRO-2,3,8,8-TETRAMETHYL-2-NAPHTALENYL)-1-ETHANONE
METHYL 2-((1RS,2RS)-3-OXO-2-PENTYLCYCLOPENTYL)ACETATE
(+−)-(E)-4-METHYL-3-DECEN-5-OL
2,4-DIMETHYL-3-CYCLOHEXENE-1-CARBALDEHYDE
1,3,3-TRIMETHYL-2-OXABICYCLO[2.2.2]OCTANE
TETRAHYDRO-4-METHYL-2-(2-METHYL-1-PROPENYL)-2H-PYRAN
ALDEHYDE C 12
1-OXA-12-CYCLOHEXADECEN-2-ONE (A) + 1-OXA-13-CYCLOHEXADECEN-2-ONE (B)
(+−)-3-(4-ISOPROPYLPHENYL)-2-METHYLPROPANAL
ALDEHYDE C 11 LENIQUE
(+−)-2,6-DIMETHYL-7-OCTEN-2-OL
(+−)-2,6-DIMETHYL-7-OCTEN-2-OL
ALLYL 3-CYCLOHEXYLPROPANOATE
(Z)-3-HEXENYL ACETATE

TABLE B-continued perfume raw materials having a Log T>-4
Perfume raw materials (Log T>-4)

(2RS,5SR)-5-METHYL-2-(2-PROPANYL)CYCLOHEXANONE (A) + (2RS,5RS)-5-
METHYL-2-(2-PROPANYL)CYCLOHEXANONE (B)
ALLYL HEPTANOATE
(1RS,2RS)-2-(2-METHYL-2-PROPANYL)CYCLOHEXYL ACETATE (A) + (1RS,2SR)-2-
(2-METHYL-2-PROPANYL)CYCLOHEXYL ACETATE (B)
1,1-DIMETHYL-2-PHENYLETHYL BUTYRATE
GERANYL ACETATE (A) + NERYL ACETATE (B)
(+-)-1-PHENYLETHYL ACETATE
1,1-DIMETHYL-2-PHENYLETHYL ACETATE
3-METHYL-2-BUTENYL ACETATE
ETHYL 3-OXOBUTANOATE (A) <=> (2Z)-ETHYL 3-HYDROXY-2-BUTENOATE (B)
8-P-MENTHANOL
8-P-MENTHANYL ACETATE (A) + 1-P-MENTHANYL ACETATE (B)
(+-)-2-(4-METHYL-3-CYCLOHEXEN-1-YL)-2-PROPANYL ACETATE
(+-)-2-METHYLBUTYL BUTANOATE
2-{(1S)-1-[(1R)-3,3-DIMETHYLCYCLOHEXYL]ETHOXY}-2-OXOETHYL PROPIONATE
3,5,6-TRIMETHYL-3-CYCLOHEXENE-1-CARBALDEHYDE (A) + 2,4,6-TRIMETHYL-3-
CYCLOHEXENE-1-CARBALDEHYDE (B)
2-CYCLOHEXYLETHYL ACETATE
ALDEHYDE C 8
ETHYL BUTANOATE
(+-)-(3E)-4-(2,6,6-TRIMETHYL-2-CYCLOHEXEN-1-YL)-3-BUTEN-2-ONE (A) + (3E)-4-
(2,6,6-TRIMETHYL-1-CYCLOHEXEN-1-YL)-3-BUTEN-2-ONE (B);
1-[(1RS,6SR)-2,2,6-TRIMETHYLCYCLOHEXYL]-3-HEXANOL
1,3,3-TRIMETHYL-2-OXABICYCLO[2.2.2]OCTANE
1,3,3-TRIMETHYL-2-OXABICYCLO[2.2.2]OCTANE
ETHYL HEXANOATE
UNDECANAL
ALDEHYDE C 10
2-PHENYLETHYL ACETATE
(1S,2S,4S)-1,7,7-TRIMETHYLBICYCLO[2.2.1]HEPTAN-2-OL (A) + (1S,2R,4S)-1,7,7-
TRIMETHYLBICYCLO[2.2.1]HEPTAN-2-OL (B)
(+-)-3,7-DIMETHYL-3-OCTANOL
1-METHYL-4-(2-PROPANYLIDENE)CYCLOHEXENE
(+)-(R)-4-(2-METHOXYPROPAN-2-YL)-1-METHYLCYCLOHEX-1-ENE
VERDYL ACETATE
(3R)-1-[(1R,6S)-2,2,6-TRIMETHYLCYCLOHEXYL]-3-HEXANOL (A) + (3S)-1-[(1R,6S)-
2,2,6-TRIMETHYLCYCLOHEXYL]-3-HEXANOL (B) + (3R)-1-[(1S,6S)-2,2,6-
TRIMETHYLCYCLOHEXYL]-3-HEXANOL (C)
(+)-(1S,1'R)-2-[1-(3,3'-DIMETHYL-1'-CYCLOHEXYL)ETHOXY]-2-METHYLPROPYL
PROPANOATE

According to an embodiment, the oil phase (or the oil-based core) comprises 2-75 wt % of a density balancing material having a density greater than 1.07 g/cm³ and 25-98 wt % of a perfume oil comprising at least 15 wt % of high impact perfume raw materials having a Log T<-4.

The density of a component is defined as the ratio between its mass and its volume (g/cm³).

Several methods are available to determine the density of a component.

One may refer for example to the ISO 298:1998 method to measure d20 densities of essential oils.

According to an embodiment, the density balancing material is chosen in the group consisting of benzyl salicylate, benzyl benzoate, cyclohexyl salicylate, benzyl phenylacetate, phenylethyl phenoxyacetate, triacetin, methyl and ethyl salicylate, benzyl cinnamate, and mixtures thereof.

According to a particular embodiment, the density balancing material is chosen in the group consisting of benzyl salicylate, benzyl benzoate, cyclohexyl salicylate and mixtures thereof.

According to a particular embodiment, the hydrophobic material is free of any active ingredient (such as perfume). According to this particular embodiment, it comprises, preferably consists of hydrophobic solvents, preferably chosen in the group consisting of isopropyl myristate, tryglycerides (e.g. Neobee® MCT oil, vegetable oils), D-limonene, silicone oil, mineral oil, and mixtures thereof with optionally hydrophilic solvents preferably chosen in the group consisting of 1,4 butanediol, benzyl alcohol, triethyl citrate, triacetin, benzyl acetate, ethyl acetate, propylene glycol (1,2-propanediol), 1,3-Propanediol, dipropylene glycol, glycerol, glycol ethers and mixtures thereof.

By "flavour ingredient or composition" it is meant here a flavouring ingredient or a mixture of flavouring ingredients, solvent or adjuvants of current use for the preparation of a flavouring formulation, i.e. a particular mixture of ingredients which is intended to be added to an edible composition or chewable product to impart, improve or modify its organoleptic properties, in particular its flavour and/or taste. Taste modulator is also encompassed in said definition. Flavouring ingredients are well known to a skilled person in the art and their nature does not warrant a detailed description here, which in any case would not be exhaustive, the skilled flavourist being able to select them on the basis of his general knowledge and according to the intended use or application and the organoleptic effect it is desired to achieve. Many of these flavouring ingredients are listed in reference texts such as in the book by S. Arctander, Perfume and Flavor Chemicals, 1969, Montclair, N.J., USA, or its more recent versions, or in other works of similar nature such as Fenaroli's Handbook of Flavor Ingredients, 1975, CRC Press or Synthetic Food Adjuncts, 1947, by M. B. Jacobs, can Nostrand Co., Inc. Solvents and adjuvants or current use for the preparation of a flavouring formulation are also well known in the art.

In a particular embodiment, the flavour is selected from the group consisting of terpenic flavours including citrus and mint oil, and sulfury flavours.

According to any one of the invention's embodiment, the oil represents between about 10% and 60% w/w, or even between 20% and 50% w/w, by weight, relative to the total weight of the slurry.

Coacervate First Material

According to an embodiment, the coacervate comprises a first polyelectrolyte and a second polyelectrolyte. According to an embodiment, the first and the second polyelectrolyte are oppositely charged.

A first polyelectrolyte (Polyelectrolyte I) of one charge, preferably selected among proteins (such as gelatin), polypeptides or polysaccharides (such as chitosan) that are able to interact with an electrolyte or polyelectrolyte that has an opposite charge to thus form a coacervate phase having the ability to coat hydrophobic interfaces in order to form the capsules. In a preferred embodiment, Polyelectrolyte I is positively charged for pH<8 and optionally forms gels or highly viscous solutions in water below the gelling temperature, and lower viscosity solutions in water at a temperature above the melting point of the gel. The viscosity above the gelling temperature is typically lower than 0.1 Pa s; below the gelling temperature, the elastic modulus G' of the gel is typically in the range 0.1-15 kPa when measured during the first 24 hours after gel formation, using the measurement methods based on shear rheometry (such methods, along with the definitions relevant for the gelling temperature, are described, for example, in Parker, A. and Normand, V., *Soft Matter*, 6, pp 4916-4919 (2010). Preferably, Polyelectrolyte I is a gelatin material.

A second polyelectrolyte (Polyelectrolyte II), which is preferably selected among polysaccharides or another polymer bearing charges of opposite sign compared to Polyelectrolyte I. Generally, Polyelectrolyte II is negatively charged for pH>2. Preferably; such polyelectrolytes are, for example, alginate salts, cellulose derivatives guar gum, pectinate salts, carrageenan, polyacrylic and methacrylic acid or xanthan gum, or yet plant gums such as acacia gum. Most preferably, it is acacia gum (gum arabic).

The ratio between polyelectrolyte 1 and polyelectrolyte 2 is preferably comprised between 10/0.1 to 0.1/10, preferably between 10/1 and 1/10 and more preferably between 6/1 and 1/6.

According to an embodiment, the first polyelectrolyte carries a net positive charge when the pH is less than 8 while the second polyelectrolyte carries a net negative charge when the pH is greater than 2.

According to an embodiment, the first polyelectrolyte is a protein chosen from the group consisting of albumins, plant proteins, vegetable globulins, gelatins and mixtures thereof.

Preferably, the protein is selected from the group consisting of a plant protein, preferably, pea proteins, soy proteins, rice proteins, wheat proteins, potato proteins, corn proteins, whey proteins, lupin proteins or mixtures thereof, or gelatin.

Preferably, the protein is selected from gelatin.

Preferably, the gelatin may be derived from fish, pork, beef, and/or poultry.

Preferably, the protein used to form the capsule wall is gelatin derived from fish, pork, beef or poultry.

According to a particular embodiment, the protein is gelatin derived from fish, preferably from warm water fish, or from pork. Warm water fish are generally known to be fish that are capable of tolerating water above 27° C. over prolonged time.

According to an embodiment, the first polyelectrolyte is gelatin and the second polyelectrolyte is selected from the group consisting of gum arabic, xanthan, alginate salts, cellulose derivatives, for example carboxymethyl cellulose, sodium carboxymethyl guar gum, pectinate salts, carrageenan, polyacrylic and methacrylic acid, xanthan gum and plant gums and/or mixtures thereof.

According to a preferred embodiment, the first polyelectrolyte is gelatin and the second polyelectrolyte is gum Arabic.

According to an embodiment, the coacervate material is present as a gel. According to a particular embodiment, the coacervate first material is a gel formed by providing conditions sufficient to induce gelation of either the first, the second, or both polyelectrolytes. Gelation may be induced by lowering the temperature below the gelling temperature of one of the polyelectrolytes, as detailed above and in the references cited in the previous section. For ionically cross-linkable polyelectrolytes such as chitosan, gelation may be induced by adding appropriate counter-ions such as tripolyphosphate.

According to a preferred embodiment, the coacervate first material is hardened chemically using a suitable cross-linker such as glutaraldehyde, glyoxal, formaldehyde, polyphenol (such as tannic acid), polyanhydrides or genipin.

Polyanhydride cross-linker can be poly(ethylene-maleic anhydride) or poly(methyl vinyl ether-maleic anhydride).

According to a particular embodiment, the coacervate first material is hardened chemically using glutaraldehyde as a cross-linker.

According to another particular embodiment, the coacervate first material is hardened enzymatically using an enzyme such as transglutaminase According to another embodiment, the coacervate is not cross-linked.

Second Polymeric Material of the Shell

According to an embodiment, the second polymeric material is selected from the group consisting of polyurea, polyurethane, polyamide, polyester, polyacrylate, polysiloxane, polycarbonate, polysulfonamide, polymers of urea and formaldehyde, melamine and formaldehyde, melamine and urea, or melamine and glyoxal and mixtures thereof.

According to a particular embodiment, the second material is polyurea and/or polyurethane.

According to an embodiment, the polymeric material is a polyurea-based material and comprises the reaction product of a polyisocyanate with optionally an amine. According this particular embodiment, interfacial polymerization can be induced by addition of a polyamine reactant. Preferably, the reactant is selected from the group consisting of water soluble guanidine salts and guanazole to form a polyurea material with the polyisocyanate. According to another embodiment, polyurea-based polymeric material is formed in absence of added polyamine reactant, and result only from the autopolymerization of the at least one polyisocyanate, preferably in the presence of a catalyst.

According to another embodiment, the polymeric material is a polyurethane-based material and comprises the reaction product of a polyisocyanate with a polyol. According to this particular embodiment, interfacial polymerization is induced by addition of a polyol reactant. Preferably the reactant is selected from the group consisting of monomeric and polymeric polyols with multiple hydroxyl groups available for reaction and mixtures thereof.

According to another embodiment, the polymeric material is a polyurea/polyurethane based material and comprises the reaction product of a polyisocyanate with a polyol and an amine. In that case interfacial polymerization is induced by addition of a mixture of the reactant mentioned under precedent first and second embodiments. Additionally, crosslinkers with both amino groups and hydroxyl groups can be used to generate polyurea/polyurethane materials. Furthermore, polyisocyanates with both urea and urethane functionalities can be used to generate polyurea/polyurethane materials.

According to another embodiment, the polymeric material is a polyamide-based material and comprises the reaction product of an acyl chloride with at least one amine, preferably at least two amines. According to a particular embodiment, the second polymeric material is a polyamide-based material as disclosed in WO2020127743A1 or WO2020127749A1, the content of which with regard to the components and method of preparation is herewith included by reference.

The definition of polyisocyanate and acyl chloride can be the definitions given later when describing the process for preparing said microcapsules.

According to an embodiment, the second material is present in an amount less than 3%, preferably less than 1% by weight based on the total weight of the microcapsule slurry. Indeed, it has been underlined that even with a reduced amount of the second material forming the wall, microcapsules still show good stability in consumer products.

Optional Components

According to an embodiment, the microcapsule slurry comprises auxiliary ingredients selected from the group of thickening agents/rheology modifiers, preservatives agents, antimicrobial agents, opacity-building agents, mica particles, salt, pH stabilizers/buffering ingredients, preferably in an amount comprised between 0 and 15%, more preferably between 0.1 and 10%, even more preferably between 0.05 and 5% by weight based on the total weight of the slurry.

Among the different thickening agents, one may cite for example anionic, cationic, non-ionic or zwitter-ionic copolymers, for instance, but not limited to polyacrylamide, polyacrylate, polyacryloyldimethyl taurate, polyquaternium-37, or carbomer and mixtures thereof. According to a particular embodiment, the thickening agent is xanthan gum, guar gum, diutan gum or mixtures thereof.

Among the different preservatives agents, one may cite for example sodium benzoate, benzisothiazolinone, methylchloroisothiazolinone, methylisothiazolinone, chlorhexidine digluconate, sodium hydroxymethylglycinate, parabens, triclosan, phenoxyethanol, caprylhydroxamic acid, potassium sorbate, lactic acid, E-polylysine, caprylyl glycol, caprylhydroxamic acid, glycerin, glyceryl caprylate, ethylhexylglycerin and mixtures thereof.

According to another embodiment, the microcapsule slurry of the invention comprises additional free (i.e non-encapsulated) perfume, preferably in an amount comprised between 5 and 50% by weight based on the total weight of the slurry.

Optional Outer Coating

According to a particular embodiment of the invention, microcapsules according to the invention comprise an outer coating material selected from the group consisting of a polysaccharide, a cationic polymer and mixtures thereof to form an outer coating to the microcapsule.

Polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose, pectin and mixtures thereof.

According to a particular embodiment, the coating consists of a cationic coating.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 2M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride.

As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

According to any one of the above embodiments of the invention, there is added an amount of polymer described above comprised between about 0% and 5% w/w, or even between about 0.1% and 2% w/w, percentage being expressed on a w/w basis relative to the total weight of the slurry. It is clearly understood by a person skilled in the art that only part of said added polymers will be incorporated into/deposited on the microcapsule shell.

Multiple Microcapsule System

According to an embodiment, the microcapsules of the invention (first microcapsule slurry) can be used in combination with a second microcapsules slurry.

Another object of the invention is a microcapsule delivery system comprising:
  the microcapsule slurry of the present invention as a first microcapsule slurry, and
  a second microcapsule slurry, wherein the microcapsules contained in the first microcapsule slurry and the second microcapsule slurry differ in their hydrophobic material and/or their wall material and/or content of wall material and/or in the curing conditions to form the wall material and/or in their coating material.

According to a particular embodiment, the second microcapsule slurry is a composite microcapsule slurry as defined in the present invention wherein the first microcapsule slurry and the second microcapsule slurry differ in the hydrophobic material and/or the first material and/or the second material and/or the ratio between the first and the second material.

As non-limiting examples, the nature of the polymeric shell of microcapsules from the second microcapsules slurry of the invention can vary. As non-limiting examples, the shell of the second microcapsules slurry can be polyurea, polyurethane, polyamide, polyacrylate, polysiloxane, polycarbonate, polysulfonamide, polymers of urea and formaldehyde, melamine and formaldehyde, melamine and urea, or melamine and glyoxal and mixtures thereof. The shell of the second microcapsules slurry can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell of the second microcapsules slurry comprises an aminoplast copolymer, such as melamine-formaldehyde or urea-formaldehyde or cross-linked melamine formaldehyde or melamine glyoxal.

According to another embodiment the shell of the second microcapsules slurry is polyurea-based made from, for example but not limited to isocyanate-based monomers and amine-containing crosslinkers such as guanidine carbonate and/or guanazole. Preferred polyurea microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). According to another embodiment, the emulsifier is an anionic or amphiphilic biopolymer preferably chosen from the group consisting of gum Arabic, soy protein, gelatin, sodium caseinate and mixtures thereof.

According to another embodiment, the shell of the second microcapsules slurry is polyurethane-based made from, for example but not limited to polyisocyanate and polyols, polyamide, polyester, etc.

According to an embodiment, the shell of the second microcapsule is a biopolymer-based shell comprising a protein.

The preparation of an aqueous dispersion/slurry of coreshell microcapsules is well known by a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Missouri U.S.A.), Cytec Industries (West Paterson, New Jersey U.S.A.), Sigma-Aldrich (St. Louis, Missouri U.S.A.).

According to a particular embodiment, the second coreshell microcapsule is a formaldehyde-free aminoplast capsule. A typical process for the preparation of formaldehyde-free aminoplast microcapsules slurry comprises the steps of
1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 1 and 600 um, and comprising:
   i. an oil;
   ii. a water medium
   iii. at least an oligomeric composition as obtained in step 1;
   iv. at least a cross-linker selected amongst
     A) $C_4$-$C_{12}$ aromatic or aliphatic di- or tri-isocyanates and their biurets, triurets, trimmers, trimethylol propane-adduct and mixtures thereof, and/or
     B) a di- or tri-oxiran compounds of formula A-(oxiran-2-ylmethyl)$_n$
       wherein n stands for 2 or 3 and 1 represents a $C_2$-$C_6$ group optionally comprising from 2 to 6 nitrogen and/or oxygen atoms;
   v. optionally a $C_1$-$C_4$ compounds comprising two $NH_2$ functional groups;
3) Heating said dispersion;
4) Cooling said dispersion.

This process is described in more details in WO 2013/068255, the content of which is included by reference.

According to another embodiment, the shell of the second microcapsules slurry is polyurea- or polyurethane-based. Examples of processes for the preparation of polyurea and polyureathane-based microcapsule slurry are for instance described in WO2007/004166, EP 2300146, EP2579976 the contents of which is also included by reference. Typically a process for the preparation of polyurea or polyurethane-based microcapsule slurry include the following steps:
   a) Dissolving at least one polyisocyanate having at least two isocyanate groups in an oil to form an oil phase;
   b) Preparing an aqueous solution of an emulsifier or colloidal stabilizer to form a water phase;
   c) Adding the oil phase to the water phase to form an oil-in-water dispersion, wherein the mean droplet size is comprised between 1 and 500 μm, preferably between 5 and 50 μm;
   d) Applying conditions sufficient to induce interfacial polymerisation and form microcapsules in form of a slurry.

Microcapsule Powder

Another object of the invention is a microcapsule powder obtained by submitting the microcapsule slurry to a drying, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, gum Arabic, vegetable gums, pectins, xanthans, alginates, carrageenans or cellulose derivatives to provide microcapsules in a powder form.

However, one may cite also other drying method such as the extrusion, plating, spray granulation, the fluidized bed, or even a drying at room temperature using materials (carrier, desiccant) that meet specific criteria as disclosed in WO2017/134179.

According to a particular embodiment, the carrier material contains free perfume oil which can be the same or different from the perfume from the core of the microcapsules.

Another object of the invention is a solid particle comprising:
  a carrier material,
  microcapsules as defined above entrapped in said carrier material, and
  optionally free perfume entrapped in said carrier material.

In a particular embodiment, the carrier material comprises a monomeric, oligomeric or polymeric carrier material, or mixtures of two or more of these.

An oligomeric carrier is a carrier wherein 2-10 monomeric units are linked by covalent bonds. For example, if the oligomeric carrier is a carbohydrate, the oligomeric carrier may be sucrose, lactose, raffinose, maltose, trehalose, fructo-oligosaccharides.

Examples of a monomeric carrier materials are glucose, fructose, mannose, galactose, arabinose, fucose, sorbitol, mannitol, for example.

Polymeric carriers have more than 10 monomeric units that are linked by covalent bonds.

In a particular embodiment, the carrier may be a polymeric carrier material. Non-limiting examples of polymeric carrier material includes polyaspartate, modified polysuccinimides, lignin and its derivatives, polyoxazoline, polyhydroxyalcanoates, polyphenols, natural and synthetic clays, polyvinyl acetates, polyvinyl alcohol, dextrines, maltodextrines, glucose syrups, natural or modified starch, polysaccharides, carbohydrates, chitosan, gum Arabic, polyethylene glycol, polyvinyl pyrrolidone, polyvinyl alcohol, acrylamides, acrylates, polyacrylic acid and related, maleic anhydride copolymers, amine-functional polymers, vinyl ethers, styrenes, polystyrenesulfonates, vinyl acids, ethylene glycol-propylene glycol block copolymers, vegetable gums, gum acacia, pectins, xanthanes, alginates, carragenans or cellulose derivatives, such as carboxymethyl methylcellulose, methylcellulose or hydroxyethyl cellulose; chitin, proteins (animal and vegetal), polyaspartate, poylsuccinimides and its derivatives, polyesters, polyaminoesters, polyhydroxyalkanoates, polycarbonates and mixtures thereof. Preferably the polymeric carrier material comprises natural or modified starch, maltodextrins, carbohydrates, chitin, proteins (animal and vegetal), polyaspartate, poylsuccinimides and its derivatives, polyesters, polyaminoesters, polyhydroxyalkanoates, polycarbonates and mixtures thereof.

According to an embodiment, the carrier material is chosen in the group consisting of polyvinyl acetate, polyvinyl alcohol, dextrins, natural or modified starch, vegetable gums, pectins, xanthans, alginates, carragenans, cellulose derivatives and mixtures thereof.

Solid particle as defined above and microcapsule powder can be used indifferently in the present invention.

Process for Preparing Microcapsule Slurry

Composite shell microcapsules according to the invention can be prepared by different processes, well-known from the person skilled in the art.

Embodiment 1

According to an embodiment, the process for preparing microcapsules as defined above, comprises the steps of:
(i) providing as a dispersion in an aqueous vehicle, a hydrophobic internal phase comprising at least a polyfunctional monomer and a hydrophobic material;
(ii) mixing a first and second polyelectrolytes in the aqueous vehicle under conditions sufficient to form a suspension of complex coacervate nodules;
(iii) depositing the complex coacervate nodules at an interface of the aqueous vehicle adjacent to the hydrophobic internal phase to form a coacervate, wherein the hydrophobic internal phase forms the core and contains the polyfunctional monomer and the hydrophobic material therein; and
(iv) providing conditions sufficient to induce interfacial polymerization to form a core-composite shell microcapsule slurry,
wherein the weight ratio between the first and second polyelectrolytes forming the coacervate and the polyfunctional monomer is comprised between 50:50 and 99.9:0.1.

According to another embodiment, the process for preparing microcapsules as defined above, comprises the steps of:
(i) providing as a dispersion in an aqueous vehicle, a hydrophobic internal phase comprising at least a polyfunctional monomer and a hydrophobic material;
(ii) mixing a first and second polyelectrolytes in the aqueous vehicle under conditions sufficient to form a suspension of complex coacervate nodules;
(iii) depositing the complex coacervate nodules at an interface of the aqueous vehicle adjacent to the hydrophobic internal phase to form a coacervate outer shell, wherein the hydrophobic internal phase forms the core and contains the polyfunctional monomer and the hydrophobic material therein; and
(iv) providing conditions sufficient to induce interfacial polymerization of the polyfunctional monomer inside the outer shell to form an inner shell at the interface between the internal phase and the outer shell to form a core-composite shell microcapsule slurry,
wherein the weight ratio between the first and second polyelectrolytes forming the coacervate and the polyfunctional monomer is comprised between 50:50 and 99.9:0.1.

Embodiment 2

According to an embodiment, the process for preparing microcapsules as defined above, comprises the steps of:
(i) mixing a first and second polyelectrolytes in an aqueous vehicle under conditions sufficient to form a suspension of complex coacervate nodules;
(ii) providing as a dispersion in the aqueous vehicle, a hydrophobic internal phase comprising at least a polyfunctional monomer and a hydrophobic material;
(iii) depositing the complex coacervate nodules at an interface of the aqueous vehicle adjacent to the hydrophobic internal phase to form a coacervate, wherein the hydrophobic internal phase forms the core and contains the polyfunctional monomer and the hydrophobic material therein; and
(iv) providing conditions sufficient to induce interfacial polymerization to form a core-composite shell microcapsule slurry, wherein the weight ratio between the first and second polyelectrolytes forming the coacervate and the polyfunctional monomer is comprised between 50:50 and 99.9:0.1.

According to another embodiment, the process for preparing microcapsules as defined above, comprises the steps of:
(i) mixing a first and second polyelectrolytes in an aqueous vehicle under conditions sufficient to form a suspension of complex coacervate nodules;
(ii) providing as a dispersion in the aqueous vehicle, a hydrophobic internal phase comprising at least a polyfunctional monomer and a hydrophobic material;
(iii) depositing the complex coacervate nodules at an interface of the aqueous vehicle adjacent to the hydrophobic internal phase to form a coacervate outer shell, wherein the hydrophobic internal phase forms the core and contains the polyfunctional monomer and the hydrophobic material therein; and
(iv) providing conditions sufficient to induce interfacial polymerization of the polyfunctional monomer inside the outer shell to form an inner shell at the interface between the internal phase and the outer shell to form a core-composite shell microcapsule slurry,
wherein the weight ratio between the first and second polyelectrolytes forming the coacervate and the polyfunctional monomer is comprised between 50:50 and 99.9:0.1.

Embodiment 3

According to an embodiment, the process for preparing microcapsules as defined above, comprises the steps of:
(i) providing as a dispersion in an aqueous vehicle comprising a first polyelectrolyte, a hydrophobic internal phase comprising at least a polyfunctional monomer and a hydrophobic material to form an oil-in-water emulsion;
(ii) adding a second polyelectrolyte in the oil-in-water emulsion
(iii) applying conditions sufficient to form a suspension of complex coacervate nodules;
(iv) depositing the complex coacervate nodules at an interface of the aqueous vehicle adjacent to the hydrophobic internal phase to form a coacervate, wherein the hydrophobic internal phase forms the core and contains the polyfunctional monomer and the hydrophobic material therein; and
(v) providing conditions sufficient to induce interfacial polymerization to form a core-composite shell microcapsule slurry,
wherein the weight ratio between the first and second polyelectrolytes forming the coacervate and the polyfunctional monomer is comprised between 50:50 and 99.9:0.1.

According to an embodiment, step (v) mentioned above is carried out before step (ii) and/or step (iii).

According to another embodiment, the process for preparing microcapsules as defined above, comprises the steps of:
(i) providing as a dispersion in an aqueous vehicle comprising a first polyelectrolyte, a hydrophobic internal phase comprising at least a polyfunctional monomer and a hydrophobic material to form an oil-in-water emulsion;
(ii) adding a second polyelectrolyte in the oil-in-water emulsion
(iii) applying conditions sufficient to form a suspension of complex coacervate nodules;
(iv) depositing the complex coacervate nodules at an interface of the aqueous vehicle adjacent to the hydrophobic internal phase to form a coacervate outer shell, wherein the hydrophobic internal phase forms the core and contains the polyfunctional monomer and the hydrophobic material therein; and
(v) providing conditions sufficient to induce interfacial polymerization interfacial polymerization of the polyfunctional monomer inside the outer shell to form an inner shell at the interface between the internal phase and the outer shell to form a core-composite shell microcapsule slurry,
wherein the weight ratio between the first and second polyelectrolytes forming the coacervate and the polyfunctional monomer is comprised between 50:50 and 99.9:0.1.

Embodiment 4

According to an embodiment, the process for preparing microcapsules as defined above, comprises the steps of:
(i) providing as a dispersion in an aqueous vehicle comprising a first polyelectrolyte, a hydrophobic internal phase comprising at least a polyfunctional monomer and a hydrophobic material to form an oil-in-water emulsion;
(ii) providing conditions sufficient to induce interfacial polymerization to form a polymeric material, preferably in the form of an inner shell
(iii) adding a second polyelectrolyte in the oil-in-water emulsion
(iv) applying conditions sufficient to form a suspension of complex coacervate nodules;
(v) depositing the complex coacervate nodules to form a coacervate, preferably in the form of a an outer coacervate shell at the interface between the continuous aqueous vehicle and the inner shell to form a core-composite shell microcapsule slurry,
wherein the weight ratio between the first and second polyelectrolytes forming the coacervate and the polyfunctional monomer is comprised between 50:50 and 99.9:0.1.

According to a particular embodiment, no amine or polyamine susceptible to polymerize with the polyfunctional monomer is added at any stage of the process.

The dispersion of the oil phase into the water phase can be carried out by different well-known techniques. As non-limiting methods, one may cite a static mixer (SMX, Sulzer, Switzerland), vibrating mixers, stirred tank reactor, Ultrasonic homogenizer, membrane emulsification device (Micropure, UK), high pressure homogenizer (APV, SPX Flow, USA), or a microfluidic emulsification device (Micronit, Netherland).

According to an embodiment, the polyfunctional monomer is chosen in the group consisting of at least one polyisocyanate, poly anhydride (such as poly maleic anhydride), poly acid chloride (i.e acyl chloride), polyepoxide, acrylate monomers, polyalkoxysilane and mixtures thereof.

According to a particular embodiment, the monomer added in step a) is at least one polyisocyanate having at least two isocyanate functional groups.

Suitable polyisocyanates used according to the invention include aromatic polyisocyanate, aliphatic polyisocyanate and mixtures thereof. Said polyisocyanate comprises at least 2, preferably at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

According to an embodiment, the polyfunctional monomer is an acyl chloride chosen in the group consisting of benzene-1,2,4-tricarbonyl trichloride, benzene-1,2,4,5-tetracarbonyl tetrachloride, cyclohexane-1,3,5-tricarbonyl trichloride, isophthalyol dichloride, terephtaloyl chloride, diglycolyl dichloride, succinic dichloride, and mixtures thereof According to a particular embodiment, the acyl chloride is 1,3,5-benzene tricarbonyl chloride.

According to a particular embodiment, the acyl chloride has the following formula (I)

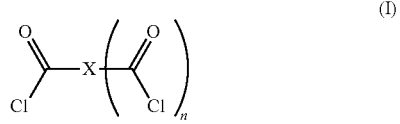

(I)

wherein n is an integer varying between 1 and 8, preferably between 1 and 6, more preferably between 1 and 4, and wherein X is either an (n+1)-valent $C_3$ to $C_6$ alkyl group, or an (n+1)-valent $C_2$ to $C_{45}$ hydrocarbon group comprising at least one group selected from (i) to (vi),

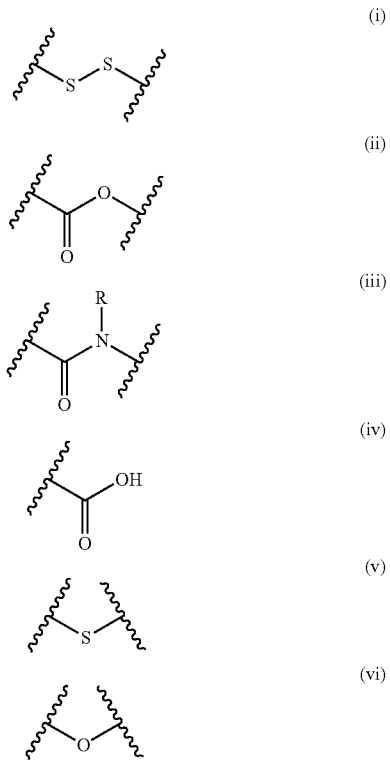

wherein R is a hydrogen atom or a methyl or ethyl group, preferably a hydrogen atom.

According to an embodiment, if the hydrocarbon group X comprises several groups selected from (i) to (vi), they are each separated by at least one carbon atom of X.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynil group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

It is understood that with the term " . . . a hydrocarbon group, possibly comprising . . . " it is meant that said hydrocarbon group optionally comprises heteroatoms to form ether, thioether, amine, nitrile or carboxylic acid groups. These groups can either substitute a hydrogen atom of the hydrocarbon group and thus be laterally attached to said hydrocarbon, or substitute a carbon atom (if chemically possible) of the hydrocarbon group and thus be inserted into the hydrocarbon chain or ring.

According to an embodiment, when group (vi) is present, it is only present in combination with either one of groups (i) to (v).

According to a particular embodiment, the acyl chloride is chosen from the group consisting of propane-1,2,3-tricarbonyl trichloride, cyclohexane-1,2,4,5-tetracarbonyl tetrachloride, 2,2'-disulfanediyldisuccinyl dichloride, 2-(2-chloro-2-oxo-ethyl)sulfanylbutanedioyl dichloride, (4-chloro-4-oxobutanoyl)-L-glutamoyl dichloride, (S)-4-((1,5-dichloro-1,5-dioxopentan-2-yl)amino)-4-oxobutanoic acid, 2,2-bis[(4-chloro-4-oxo-butanoyl)oxymethyl]butyl 4-chloro-4-oxo-butanoate, [2-[2,2-bis[(4-chloro-4-oxo-butanoyl)oxymethyl]butoxymethyl]-2-[(4-chloro-4-oxo-butanoyl)oxymethyl]butyl] 4-chloro-4-oxo-butanoate, 2,2-bis[(2-chlorocarbonylbenzoyl)oxymethyl]butyl 2-chlorocarbonyl-benzoate, [2-[2,2-bis[(2-chlorocarbonyl-benzoyl)oxymethyl]butoxymethyl]-2-[(2-chlorocarbonyl-benzoyl)oxymethyl]butyl] 2-chlorocarbonylbenzoate, 4-(2,4,5-trichlorocarbonylbenzoyl)oxybutyl 2,4,5-trichlorocarbonyl-benzoate, and mixtures thereof.

According to an embodiment, the monomer used in the process of the invention is present in amounts representing from 0.1 and 15%, preferably from 0.5 and 3% by weight based on the total amount of the oil phase.

According to anyone of the preceding embodiments, in addition to the polyfunctional monomer present hydrophobic internal phase, the aqueous vehicle may comprise an aminoresin.

According to anyone of the preceding embodiments, the hydrophobic internal phase is free of at least one polyfunctional monomer and the aqueous vehicle may comprise an aminoresin.

According to this embodiment, the weight ratio between the first and second polyelectrolytes and the aminoresin is comprised between 50:50 and 99.9:0.1.

All the embodiments described previously for the microcapsule slurry also apply for the process for preparing said microcapsules.

Another object of the invention is a microcapsule slurry obtainable by the process described previously.

Perfuming Composition/Consumer Products

The microcapsules of the invention can be used in combination with active ingredients.

An object of the invention is therefore a composition comprising:
(i) microcapsules or microcapsule slurry as defined above;
(ii) an active ingredient, preferably chosen in the group consisting of a cosmetic ingredient, skin caring ingredient, perfume ingredient, flavor ingredient, malodour counteracting ingredient, bactericide ingredient, fungicide ingredient, pharmaceutical or agrochemical ingredient, a sanitizing ingredient, an insect repellent or attractant, and mixtures thereof.

The microcapsules of the invention can also be added in different perfumed consumer products.

In particular a perfuming composition comprising (i) microcapsules or microcapsule slurry as defined above; (ii) at least one perfuming co-ingredient; and (iii) optionally a perfumery adjuvant, is another object of the invention.

By "perfuming co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor. The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30%, preferably between 0.1 and 20%, by weight of microcapsules slurry as defined above.

The invention's microcapsules can advantageously be used in many application fields and used in consumer products. Microcapsules can be used in liquid form applicable to liquid consumer products as well as in powder form, applicable to powder consumer products.

In the case of microcapsules including a perfume oil-based core, the products of the invention, can in particular be of use in perfumed consumer products such as products belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsules than those here-disclosed.

In particular a liquid consumer product comprising:
from 2 to 65% by weight, relative to the total weight of the consumer product, of at least one surfactant;
water or a water-miscible hydrophilic organic solvent; and
a perfuming composition, microcapsules or microcapsule slurry as defined above, wherein the active ingredient comprise a perfume is another object of the invention.

Also a powder consumer product comprising
from 2 to 65% by weight, relative to the total weight of the consumer product, of at least one surfactant; and a perfuming composition, microcapsules or microcapsule slurry, wherein the active ingredient comprise a perfume as defined above is part of the invention.

According to a particular embodiment, the process for preparing the microcapsules contained in the perfumed consumer product comprises the addition of a polyisocyanate into the oil phase to improve the stability in challenging bases comprising a high amount of surfactants.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumed consumer product can be a perfume, such as a fine perfume, a cologne, an after-shave lotion, a body-splash; a fabric care product, such as a liquid or solid detergent, tablets and pods, a fabric softener, a dryer sheet, a fabric refresher, an ironing water, or a bleach; a personal-care product, such as a hair-care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or powder or tablet dishwashing products, toilet cleaners or products for cleaning various surfaces, for example sprays & wipes intended for the treatment/refreshment of textiles or hard surfaces (floors, tiles, stone-floors etc.); a hygiene product such as sanitary napkins, diapers, toilet paper.

Another object of the invention is a consumer product comprising:
a personal care active base, and
microcapsules or microcapsule slurry or microcapsule powder as defined above or the perfuming composition as defined above,
wherein the consumer product is in the form of a personal care composition.

Personal care active base in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

The personal care composition is preferably chosen in the group consisting of a hair-care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product) or a fine fragrance product (e.g. Eau de Toilette—EdT).

Another object of the invention is a consumer product comprising:
a home care or a fabric care active base, and
microcapsules or microcapsule slurry or microcapsule powder as defined above or the perfuming composition as defined above,
wherein the consumer product is in the form of a home care or a fabric care composition. Home care or fabric care bases in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature. The home or fabric care composition is preferably chosen in the group consisting fabric softener, liquid detergent, powder detergent, liquid scent booster solid scent booster.

All of the embodiments described previously regarding the microcapsule slurry (regarding for example the hydrophobic material, the first and second material) also apply for the consumer products disclosed above and below.

Fabric Softener

An object of the invention is a consumer product in the form of a fabric softener composition comprising:
a fabric softener active base; preferably chosen in the group consisting of dialkyl quaternary ammonium salts, dialkyl ester quaternary ammonium salts (esterquats), Hamburg esterquat (HEQ), TEAQ (triethanolamine quat), silicones and mixtures thereof, and
a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material.

According to an embodiment, the consumer product in the form of a fabric softener composition and comprises:
between 85 and 99.95% of a fabric softener active base; preferably chosen in the group consisting of dialkyl quaternary ammonium salts, dialkyl ester quaternary ammonium salts (esterquats), Hamburg esterquat (HEQ), TEAQ (triethanolamine quat), silicones and mixtures thereof, by weight based on the total weight of the composition
between 0.05 to 15 wt %, more preferably between 0.1 and 5 wt % by weight of a composite microcapsule slurry comprising at least one microcapsule having:
an oil-based core comprising an hydrophobic material, preferably a perfume a composite shell comprising a first material and a second material, wherein:
the first material and the second material are different,
the first material is a coacervate, and
the second material is a polymeric material,
the weight ratio in the slurry between the first material and the second material is comprised between 50:50 and 99.9:0.1.

Liquid Detergent

An object of the invention is a consumer product in the form of a liquid detergent composition comprising:
a liquid detergent active base; preferably chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, and mixtures thereof and
a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material.

According to an embodiment, the consumer product in the form of a liquid detergent composition and comprises:
between 85 and 99.95% of a liquid detergent active base; preferably chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, by weight based on the total weight of the composition
between 0.05 to 15 wt %, more preferably between 0.1 and 5 wt % by weight of a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material,
the weight ratio in the slurry between the first material and the second material is comprised between 50:50 and 99.9:0.1.

Solid Detergent

An object of the invention is a consumer product in the form of a solid detergent composition comprising:
a solid detergent active base; preferably chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, and
a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material.

According to an embodiment, the consumer product in the form of a solid detergent composition and comprises:
between 85 and 99.95% of a solid detergent active base; preferably chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, by weight based on the total weight of the composition
between 0.05 to 15 wt %, more preferably between 0.1 and 5 wt % by weight of the composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material,
the weight ratio in the slurry between the first material and the second material is comprised between 50:50 and 99.9:0.1.

Shampoo/Shower Gel

An object of the invention is a consumer product in the form of a shampoo or a shower gel composition comprising:
a shampoo or a shower gel active base; preferably chosen in the group consisting of sodium alkylether sulfate, ammonium alkylether sulfates, alkylamphoacetate, cocamidopropyl betaine, cocamide MEA, alkylglucosides and aminoacid based surfactants and mixtures thereof, and
a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material.

According to an embodiment, the consumer product in the form of a shampoo or a shower gel composition and comprises:

between 85 and 99.95% of a shampoo or a shower gel active base; preferably chosen in the group consisting of sodium alkylether sulfate, ammonium alkylether sulfates, alkylamphoacetate, cocamidopropyl betaine, cocamide MEA, alkylglucosides and aminoacid based surfactants and mixtures thereof, by weight based on the total weight of the composition between 0.05 to 15 wt %, more preferably between 0.1 and 5 wt % by weight of a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material,
the weight ratio in the slurry between the first material and the second material is comprised between 50:50 and 99.9:0.1.

Rinse-Off Conditioner

An object of the invention is a consumer product in the form of a rinse-off conditioner composition comprising:
a rinse-off conditioner active base; preferably chosen in the group consisting of one or more quaternary ammonium compounds, preferably chosen in the group consisting of cetyltrimonium chloride, stearyl trimonium chloride, benzalkonium chloride, behentrimonium chloride and mixture thereof, and
a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material.

According to an embodiment, the consumer product in the form of a rinse-off conditioner composition comprises:
between 85 and 99.95% of a rinse-off conditioner active base; preferably chosen in the group consisting of cetyltrimonium chloride, stearyl trimonium chloride, benzalkonium chloride, behentrimonium chloride and mixture thereof, by weight based on the total weight of the composition
between 0.05 to 15 wt %, more preferably between 0.1 and 5 wt % by weight of a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate,
the second material is a polymeric material,
the weight ratio in the slurry between the first material and the second material is comprised between 50:50 and 99.9:0.1.

Hair Coloration

An object of the invention is a consumer product in the form of an oxidative hair coloring composition comprising:
an oxidizing phase comprising an oxidizing agent and an alkaline phase comprising an alkaline agent, a dye precursor and a coupling compound; wherein said dye precursor and said coupling compound form an oxidative hair dye in the presence of the oxidizing agent, and
a composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is polymeric material.

According to an embodiment, the consumer product in the form of an oxidative hair coloring composition comprising:
between 85 and 99.9% of an oxidizing phase comprising an oxidizing agent and an alkaline phase comprising an alkaline agent, a dye precursor and a coupling compound; wherein said dye precursor and said coupling compound form an oxidative hair dye in the presence of the oxidizing agent, by weight based on the total weight of the composition
between 0.05 to 15 wt %, more preferably between 0.1 and 5 wt % by weight of the composite microcapsule slurry comprising at least one microcapsule having:
an oil-based core comprising an hydrophobic material, preferably a perfume
a composite shell comprising a first material and a second material, wherein:
the first material and the second material are different,
the first material is a coacervate, and
the second material is a polymeric material,
the weight ratio in the slurry between the first material and the second material is comprised between 50:50 and 99.9:0.1.

By "oxidative hair coloring composition", it is meant a composition comprising two groups of colorless dye molecules: the dye precursor and the coupling agent. Upon reaction with each other through an oxidation process, they form a wide range of colored molecules (dyes) that are then trapped into the hair due their size. In other words, the dye precursor and the coupling compound form an oxidative hair dye in the presence of the oxidizing agent.

"Dye precursor" and "oxidative dye precursor" are used indifferently in the present invention.

Dye precursors can be aromatic compounds derived from benzene substituted by at least two electron donor groups such as $NH_2$ and OH in para or ortho positions to confer the property of easy oxidation.

According to an embodiment, dye precursors are chosen in the group consisting of p-phenylene diamine, 2,5-diamino toluene, N,N-bis(2-hydroxymethyl)-p-phenylene diamine, 4-aminophenol, 1,4-diamino-benzene, and mixtures thereof.

The primary dye precursors is used in combination with coupling agents. Coupling agents are preferably aromatic compounds derived from benzene and substituted by groups such as $NH_2$ and OH in the meta position and do not produce color singly, but which modify the color, shade or intensity of the colors developed by the dye precursor.

According to an embodiment, the coupling agent is chosen in the group consisting of resorcinol, 2-methyl resorcinol, 4-chlororesorchinol, 2,5-diamino-toluene, 1,3-diamino-benzene, 2,4-diaminophenoxyethanol HCl, 2-amino-hydroxyethylaminoanisole sulfate, 4-amino-2-hydroxytoluene, and mixtures thereof.

The oxidative dye precursor is preferably used in an amount comprised between 0.001% and 5%, preferably between 0.1% and 4% by weight based on the total weight of the composition.

The use of oxidative dye precursors and coupling agents in hair coloring formulation have been widely disclosed in the prior art and is well-known from the person skilled in the art. One may cite for example EP0946133A1, the content of which is incorporated by reference.

The alkaline phase comprises an alkaline agent, preferably chosen in the group consisting of ammonia hydroxide, ammonia carbonate, ethanolamine, potassium hydroxide, sodium borate, sodium carbonate, triethanolamine and mixtures thereof.

The alkaline agent is preferably used in an amount comprised between 1% and 10%, preferably between 3% and 9% by weight based on the total weight of the composition.

According to the invention, the coupling agent and the dye precursor in an alkaline medium form an oxidative hair dye in the presence of the oxidizing agent.

The oxidizing agent will supply the necessary oxygen gas to develop color molecules and create a change in hair color.

The oxidizing agent should be safe and effective for use in the compositions herein.

Preferably, the oxidizing agents suitable for use herein will be soluble in the compositions according to the present invention when in liquid form and/or in the form intended to be used.

Preferably, oxidizing agents suitable for use herein will be water-soluble. Suitable oxidizing agents for use herein are selected from inorganic peroxygen oxidizing agents, pre-formed organic peroxyacid oxidizing agents and organic peroxide oxidizing agents or mixtures thereof.

The oxidizing agent is preferably used in an amount comprised between 5 and 30%, preferably between 5 and 25% by weight based on the total weight of the composition.

Components commonly used in cosmetic compositions may be added into the hair coloring composition as defined in the present invention. One may cite for example, surfactants, cationic polymers, oily substances, silicone derivatives, free perfume, preservatives, ultraviolet absorbents, antioxidants, germicides, propellants, thickeners.

According to a particular embodiment, the hair coloring composition comprises one or more quaternary ammonium compounds, preferably chosen in the group consisting of cetyltrimonium chloride, stearyl trimonium chloride, benzalkonium chloride, behentrimonium chloride and mixture thereof to confer hair conditioner benefits.

Perfuming Composition

According to a particular embodiment, the consumer product is in the form of a perfuming composition comprising:

0.1 to 30%, preferably 0.1 to 20% of microcapsules as defined previously, 0 to 40%, preferably 3-40% of perfume, and 20-90, preferably 40-90% of ethanol, by weight based on the total weight of the perfuming composition.

The invention will now be further described by way of examples. It will be appreciated that the invention as claimed is not intended to be limited in any way by these examples.

EXAMPLES

General Protocol for Preparing Microcapsules A-I
Protocol 1

Aqueous solutions of 10% wt. gelatine (A) (pork or fish), and 10% wt. gum Arabic (B) are prepared separately.

The fragrance (Perfume A—see composition in Table 1) to be encapsulated is mixed with a given amount of poly-isocyanate (trimethylol propane-adduct of xylylene diisocyanate Takenate® D-110N, Mitsui Chemical) (C).

In a vessel at 40° C., the solution (A) and the solution (B) are added to warm demineralised water under mechanical shear. pH is adjusted to 4.45 using an acid. The mixture is maintained at 40° C. during 15 min.

The solution (C) is slowly added to the mixture and emulsified/homogenised by mechanical shear forces (impeller, disperser, turbine etc. . . . ) at a given rate to reach the desired average droplet size. Mechanical shear is maintained at the same rate and the solution is then subjected to a thermal treatment at 50-90° C. After a duration between 30 to 240 min, the mixture is cooled down to 10° C. at a controlled rate between 0.2 and 0.3° C. min$^{-1}$. The stirring speed is slightly decreased, and a cross-linking agent (glutaraldehyde aq.50% wt. Supplied by Sigma-Aldrich) is finally added to the mixture. The capsule suspension is mixed during 4 to 10 hours at 20-25° C. to allow a complete reaction.

The result is an aqueous suspension of microcapsules.
Protocol 2

Aqueous solutions of 10% wt. gelatine (A) (pork or fish), and 10% wt. gum Arabic (B) are prepared separately.

The fragrance (Perfume A—see composition in Table 1) to be encapsulated is mixed with a given amount of poly-isocyanate (trimethylol propane-adduct of xylylene diisocyanate, Takenate® D-110N, Mitsui Chemical) (C).

In a vessel at 40° C., the solution (A) and the solution (B) are added to warm demineralised water under mechanical shear.

The solution (C) is slowly added to the mixture and emulsified/homogenised by mechanical shear forces (impeller, disperser, turbine etc. . . . ) at a given rate to reach the desired average droplet size. pH is adjusted to 4.45 using an acid. The mixture is kept at 40° C. during 15 min. Mechanical shear is maintained at the same rate and the solution is then subjected to a thermal treatment at 50-90° C. After a duration between 30 to 240 min, the mixture is cooled down to 10° C. at a controlled rate between 0.2 and 0.3° C. min$^{-1}$. The stirring speed is slightly decreased, and a cross-linking agent (glutaraldehyde aq.50% wt. Supplied by Sigma-Aldrich) is finally added to the mixture. The capsule suspension is mixed during 4 to 10 hours at 20-25° C. to allow a complete reaction.

The result is an aqueous suspension of microcapsules.
Protocol 3

An aqueous solution of 10% wt. gelatine (A) (pork or fish) is prepared separately.

A fragrance (Perfume A—see composition in Table 1) to be encapsulated is mixed with poly-isocyanate (trimethylol propane-adduct of xylylene diisocyanate, Takenate® D-110N, Mitsui Chemical) (B).

Gum Arabic is dissolved in demineralised water to form the aqueous phase. The mixture is stirred until complete solubilisation and warmed at 40° C. Solution (B) is dispersed in the aqueous phase and emulsified by mechanical shear, static mixer, rotor-stator or rotor-rotor to obtain the desired particle size. Solution (A) is then added to the mixture under continued mechanical shear, the pH is adjusted to 4.45 using an acid and maintained as such during 10 min. Mechanical shear is maintained at the same rate and the solution is then subjected to a thermal treatment at 50-90° C. After a duration between 30 to 240 min, the mixture is cooled down to 10° C. at a controlled rate between 0.2 and 0.3° C. min$^{-1}$. The stirring speed is slightly decreased, and a cross-linking agent (glutaraldehyde aq.50% wt. Supplied by Sigma-Aldrich) is finally added to the mixture. The capsule suspension is mixed during 4 to 10 hours at 20-25° C. to allow a complete reaction.

The result is an aqueous suspension or slurry of microcapsules.

Protocol 4

An aqueous solution of 10% wt. gelatine (A) (pork or fish) is prepared separately.

A fragrance (Perfume A—see composition in Table 1) to be encapsulated is mixed with poly-isocyanate (trimethylol propane-adduct of xylylene diisocyanate, Takenate® D-110N, Mitsui Chemical) (B).

Gum Arabic is dissolved in demineralised water to form the aqueous phase. The mixture is stirred until complete solubilisation and warmed at 40° C. Solution (B) is dispersed in the aqueous phase and emulsified by mechanical shear, static mixer, rotor-stator or rotor-rotor to obtain the desired particle size.

The solution is then subjected to a thermal treatment at 50-90° C. during 30 to 240 min, the mixture is cooled down to 40° C., Solution (A) is then added to the mixture under continued mechanical shear, the pH is adjusted to 4.45 using an acid and maintained as such during 10 min. The mixture is cooled down at a controlled rate between 0.2 and 0.3° C. min$^{-1}$. The stirring speed is slightly decreased, and a cross-linking agent (glutaraldehyde aq.50% wt. Supplied by Sigma-Aldrich) is finally added to the mixture. The capsule suspension is mixed during 4 to 10 hours at 20-25° C. to allow a complete reaction.

The result is an aqueous suspension or slurry of microcapsules.

Protocol 5

Aqueous solution of 2% wt. chitosan in HCl (pH=2) (A) is prepared separately. A fragrance (Perfume A—see composition in Table 1) to be encapsulated is mixed with poly-isocyanate (trimethylol propane-adduct of xylylene diisocyanate, Takenate® D-110N, Mitsui Chemical) (B).

Gum Arabic is dissolved in demineralised water to form the aqueous phase and adjusted at a pH=2 using HCl 1M. The mixture is stirred until complete solubilisation. Solution (B) is dispersed in the aqueous phase and emulsified by mechanical shear, static mixer, rotor-stator or rotor-rotor to obtain the desired particle size. Solution (A) is then added to the mixture under continued mechanical shear. The pH is then adjusted to 4.0 by addition of Triethanolamine 20 wt aq. at a controlled rate between 1 and 50 ml/min, the solution is maintained as such during 10 min. Mechanical shear is maintained at the same rate and the solution is then subjected to a thermal treatment at 50-90° C. After a duration between 30 to 240 min, the mixture is cooled down to room temperature at a controlled rate between 0.2 and 0.3° C. min$^{-1}$. The stirring speed is slightly decreased, and a cross-linking agent (glutaraldehyde aq.500 wt. Supplied by Sigma-Aldrich) is finally added to the mixture. The capsule suspension is mixed during 4 to 10 hours at 20-25° C. to allow a complete reaction.

The result is an aqueous suspension or slurry of microcapsules.

TABLE 1

Perfume oil A

| Ingredients | % in oil |
|---|---|
| Ethyl 2-methyl-pentanoate | 3.20% |
| Eucalyptol | 7.80% |
| 2,4-Dimethyl-3-cyclohexene-1-carbaldehyde [1] | 0.75% |
| Aldehyde $C_{10}$ | 0.75% |
| Citronellyl Nitrile | 4.30% |
| Isobornyl acetate | 3.00% |
| 2-tert-butyl-1-cyclohexyl acetate [2] | 9.80% |
| Citronellyl Acetate | 1.30% |
| 2-Methylundecanal | 3.00% |
| Diphenyloxide | 0.80% |
| Aldehyde $C_{12}$ | 1.30% |
| Dicyclopentadiene acetate | 9.85% |
| Ionone beta | 3.30% |
| Undecalactone gamma | 18.75% |
| Hexyl Salicylate | 15.90% |
| Benzyl Salicylate | 16.20% |
| TOTAL | 100% |

[1] Origin: Firmenich SA, Geneva, Switzerland
[2] Origin: IFF;

Example 1

Preparation of Microcapsules Slurry

Microcapsules A-H have been prepared by using Protocol 3. Similar results have been obtained by using Protocol 1, 2 and 4.

TABLE 2

Microcapsules compositions

| Components | A | B | C | D |
|---|---|---|---|---|
| Water | 74.8 | 74.8 | 74.7 | 75.8 |
| Gum arabic[1] | 1.1 | 1.1 | 1.1 | 0.6 |
| Gelatine[2] | 1.1 | 1.1 | 1.1 | 0.6 |
| Perfume A[3] | 22.1 | 22.1 | 22.1 | 22.2 |
| Takenate ®[4] | 0.33 | 0.40 | 0.44 | 0.33 |
| Lactic acid[5] | 0.5 | 0.5 | 0.5 | 0.5 |
| Glutaraldehyde[6] | 0.04 | 0.04 | 0.04 | 0.02 |
| Particle size (microns) | 44 | 72 | 68 | 32 |
| Weight ratio in the slurry between coacervate and polyisocyanate | 90:10 | 88:12 | 87:13 | 83:17 |
| Weight concentration of the polyisocyanate in the slurry | 0.25% | 0.30% | 0.33% | 0.25% |

[1] Nexira
[2] PB Leiner
[3] See table 1
[4] Trimethylol propane-adduct of xylylene diisocyanate, origin: Mitsui Chemicals, Inc., Japan, 75% solution of polyisocyanate in ethyl acetate
[5] Purac Biochem, 90% aqueous solution
[6] Sigma Aldrich, 50% aqueous solution

TABLE 3

Microcapsules compositions

| Components | E | F | G | H |
|---|---|---|---|---|
| Water | 74.8 | 74.8 | 74.7 | 74.6 |
| Gum arabic[1] | 1.3 | 0.9 | 1.1 | 1.1 |
| Gelatine[2] | 0.9 | 1.3 | 1.1 | 1.1 |
| Perfume A[3] | 22.1 | 22.1 | 22.1 | 22.1 |
| Takenate ®[4] | 0.40 | 0.40 | 0.48 | 0.55 |
| Lactic acid[5] | 0.5 | | 0.5 | 0.5 |
| Hydrochloric Acid[7] | | 0.5 | | |
| Glutaraldehyde[6] | 0.04 | 0.05 | 0.04 | 0.04 |
| Particle size | 28 | 70 | 34 | 30 |

TABLE 3-continued

Microcapsules compositions

| Components | E | F | G | H |
|---|---|---|---|---|
| Weight ratio in the slurry between coacervate and polyisocyanate | 88:12 | 88:12 | 86:14 | 84:16 |
| Weight concentration of the polyisocyanate in the slurry | 0.30% | 0.30% | 0.36% | 0.41% |

[1] Nexira
[2] PB Leiner
[3] See table 1
[4] Trimethylol propane-adduct of xylylene diisocyanate, origin: Mitsui Chemicals, Inc., Japan, 75% solution in ethyl acetate
[5] Purac Biochem, 90% aqueous solution
[6] Sigma Aldrich, 50% aqueous solution
[7] SigmaAldrich, 1M Microcapsules I have been prepared by using protocol 5.

TABLE 4

Microcapsules compositions

| Components | I |
|---|---|
| Water | 76.35 |
| Gum arabic [1] | 2.01 |
| Chitosan [2] | 0.40 |
| Perfume A [3] | 16.75 |
| Takenate ® [4] | 0.17 |
| Hydrochloric Acid [5] | 2 |
| Triethanolamine [6] | 0.5 |
| Glutaraldehyde [7] | 0.08 |
| Particle size | 35 |
| Weight ratio in the slurry between coacervate and polyisocyanate | 95:05 |
| Weight concentration of the polyisocyanate in the slurry | 0.13% |

[1] Nexira
[2] Sigma Aldrich, medium molecular weight
[3] See table 1
[4] Trimethylol propane-adduct of xylylene diisocyanate, origin: Mitsui Chemicals, Inc., Japan, 75% solution in ethyl acetate
[5] Sigma Aldrich, 1M
[6] Sigma Aldrich, 1M
[7] Sigma Aldrich, 50% aqueous solution Particle size was determined on a Mastersizer 3000 (Dv (50)).

Some of the microcapsules slurries (A-H) were mixed then with preservatives and thickening polymers (0.5% sodium benzoate and 0.1 to 0.5% xanthan gum).

Example 2

Preparation of Microcapsules Slurry
Preparation of microcapsules J

Benzene-1,3,5-tricarbonyl chloride (1.77 g) is dissolved in benzyl benzoate (3 g). Sodium caseinate (2 g) is dispersed in benzyl benzoate (7 g) and was optionally maintained under stirring at 60° C. for one hour. Both solutions are mixed together, stirred at room temperature for 10 minutes, and then added to a perfume oil (25 g) at room temperature to form an oil phase. Oil phase was mixed in water (94 g) containing L-Lysine (2 g). Reaction mixture is stirred with an Ultra Turrax at 24,000 rpm for 30 s or 1 minute to afford an emulsion. Ethylenediamine (0.2 g) is dissolved in water (5 g) and this solution is added dropwise to the emulsion. The reaction mixture is stirred at 40° C. for 4 h to afford a white dispersion. 30 g of an aqueous solution of 10% wt. Fish gelatin and Gum Arabic (2/1) is prepared separately and warmed at 40° C. The dispersion is then added at a controlled rate to the gelatin/gum Arabic mixture, until the pH reaches 4.58, the mixture is then cooled down to 10° C. at a controlled rate between 0.2 and 0.3° C. min$^{-1}$.

Optionally a cross-linking agent can be added to the mixture and mixed during 4 to 10 hours at 20-25° C. to allow a complete reaction.

The result is an aqueous suspension or slurry of microcapsules.

Preparation of Microcapsules K

Benzene-1,3,5-tricarbonyl chloride (1.77 g) is dissolved in benzyl benzoate (3 g). Sodium caseinate (2 g) is dispersed in benzyl benzoate (7 g) and was optionally maintained under stirring at 60° C. for one hour. Both solutions are mixed together, stirred at room temperature for 10 minutes, and then added to a perfume oil (25 g) at room temperature to form an oil phase. Oil phase is mixed in water (94 g) containing L-Lysine (2 g). Reaction mixture is stirred with an Ultra Turrax at 24,000 rpm for 30 s or 1 minute to afford an emulsion. Ethylenediamine (0.2 g) is dissolved in water (5 g) and this solution is added dropwise to the emulsion. The reaction mixture is stirred at 40° C. for 4 h to afford a white dispersion. An aqueous solution of 10% wt. Fish gelatin and Gum Arabic (2/1) is prepared separately and warmed at 40° C. 45 g of this mixture is added to the dispersion, the pH is adjusted to 4.58, and the mixture is then cooled down to 10° C. at a controlled rate between 0.2 and 0.3° C. min$^{-1}$. Optionally a cross-linking agent can be added to the mixture and mixed during 4 to 10 hours at 20-25° C. to allow a complete reaction.

The result is an aqueous suspension or slurry of microcapsules.

Preparation of Microcapsules L and M

Microcapsules L and M were prepared using respectively the process for preparing microcapsules J and K expect that diethylene triamine (0.2 g) is added with ethylenediamine in the water phase.

Preparation of Microcapsules N

Benzene-1,3,5-tricarbonyl chloride (1.77 g) is dissolved in perfume oil (30 g) to form an oil phase. Oil phase is mixed in water (97 g) containing gum Arabic (3 g). Reaction mixture is stirred with an Ultra Turrax at 24,000 rpm for 30 s or 1 minute to afford an emulsion. m-XDA (8.04 g) was dissolved in water (5 g) and this solution is added dropwise to the emulsion. The reaction mixture was stirred at 200 rpm at 40° C. for 4 h to afford a white dispersion.

An aqueous solution of 10% wt. Fish gelatin is prepared separately and added (45 g) to the white dispersion, the pH is adjusted to 4.55 and the mixture is cooled down to 10° C. at a controlled rate between 0.2 and 0.3° C. min-1.

Optionally a cross-linking agent can be added to the mixture and mixed during 4 to 10 hours at 20-25° C. to allow a complete reaction.

The result is an aqueous suspension or slurry of microcapsules.

Preparation of Microcapsules O

Benzene-1,3,5-tricarbonyl chloride (1.77 g) is dissolved in perfume oil (30 g) to form an oil phase. Oil phase was mixed in water (97 g) containing gum Arabic (3 g). Reaction mixture was stirred with an Ultra Turrax at 24,000 rpm for 30 s or 1 minute to afford an emulsion. m-XDA (8.04 g) is dissolved in water (5 g) and this solution was added dropwise to the emulsion. The reaction mixture is stirred at 200 rpm at 40° C. for 4 h to afford a white dispersion. 45 g of an aqueous solution of 10% wt. Fish gelatin is prepared separately and warmed at 40° C. The dispersion is then added at a controlled rate to the gelatin solution, the pH is adjusted to 4.55 and finally the mixture is cooled down to 10° C. at a controlled rate between 0.2 and 0.3° C. min-1. Optionally a cross-linking agent can be added to the mixture and mixed during 4 to 10 hours at 20-25° C. to allow a complete reaction.

The result is an aqueous suspension or slurry of microcapsules.

Example 3

Stability Performance in a Fabric Softener Composition

Capsules of the present invention were dispersed in fabric softener base described in table 5 to obtain a concentration of encapsulated perfume oil at 0.22% and stability was evaluated after 1 month at the elevated temperature of 37° C.

TABLE 5

Fabric Softener composition

| Product | Wt % |
|---|---|
| Stepantex VL 90A | 8.88 |
| Calcium Chloride Sol. 10% | 0.36 |
| Proxel GXL | 0.04 |
| Perfume | 1 |
| Water | 89.72 |
| TOTAL | 100 |

Protocol for the Stability Assessment

Weigh 1 g of sample into a 20 mL scintillation vial. Add 4 mL of water and mix for 5 min at 480 rpm on an IKA KS130 orbital shaker. Add 5 mL of extraction solvent (90% isooctane/10% ether with 150 ppm 1,4-dibromobenzene) and mix for 15 min at 480 rpm on an IKA KS130 orbital shaker. Transfer to a 15 mL centrifuge tube and spin for 60 min at 6000 rcf. Analyze the supernatant with a Shimatzu GCMS (model) or equivalent. All samples are compared to a free oil reference control which corresponds to 100% leakage.

Figure 2:
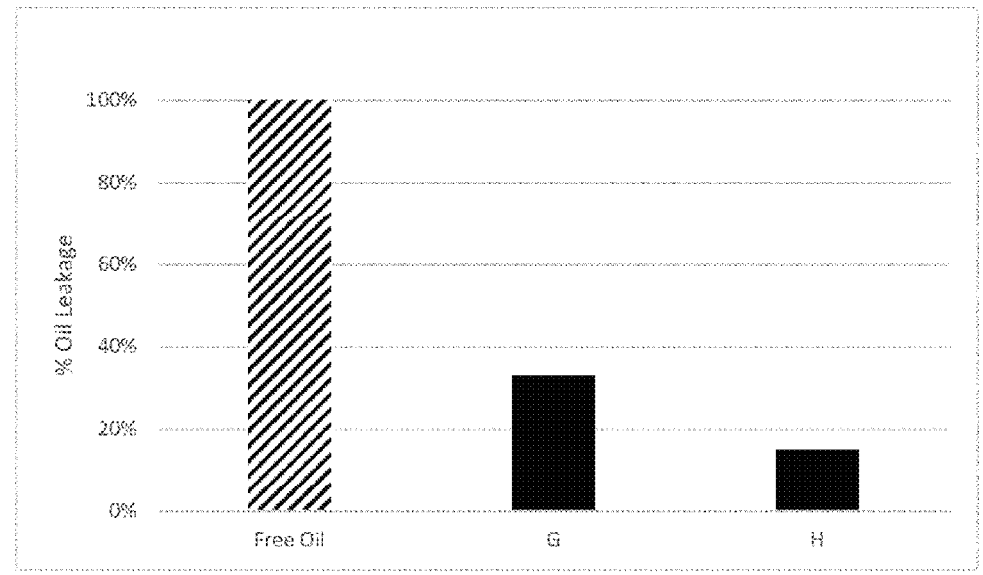

Results are shown in FIG. 1 and FIG. 2.

One can conclude from FIG. 1 and FIG. 2, that even with the limited amount of polyisocyanate, microcapsules of the invention exhibit significant encapsulation and stabilization of fragrance oil. The capsules retain significant oil after incubation in harsh and complex application formulations for 1 month at 37° C., which serves as an accelerated stability test indicative of longer term stability and performance. Stability results are plotted against the equivalent loading of free perfume oil in fabric softener applications.

Example 4

Olfactive Performance in a Fabric Softener Composition

A load of towels (24) was washed with 36 g of unperfumed detergent followed by 15 g of fabric softener (see table 5) loaded with 0.116% encapsulated oil (perfume A), and the towels were line-dried for 24 hours. Panelists evaluated their own set of towels and rated fragrance intensity before and after rubbing on an anchored linear labeled line scale.

Evaluation Scale:
1=no odor; 2=just perceptible; 3=weak; 4=moderate; 5=strong; 6=very strong; 7=Extremely Strong Results The intensity of the perception of the perfume on dried towels treated with the microcapsules was evaluated by a panel of 17 to 18 trained panelists. They were asked to rate the intensity of the perfume perception on a scale ranging from 1 to 7, wherein 1 means no odour and 7 means very strong odour.

Figure 3:
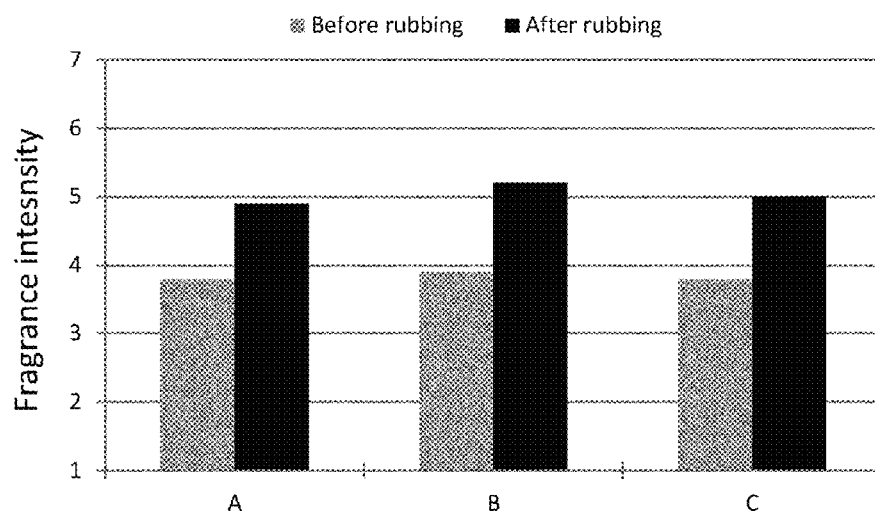
FIG. 3 represents olfactive performance of microcapsules according to the invention in a fabric softener.
Figure 4:
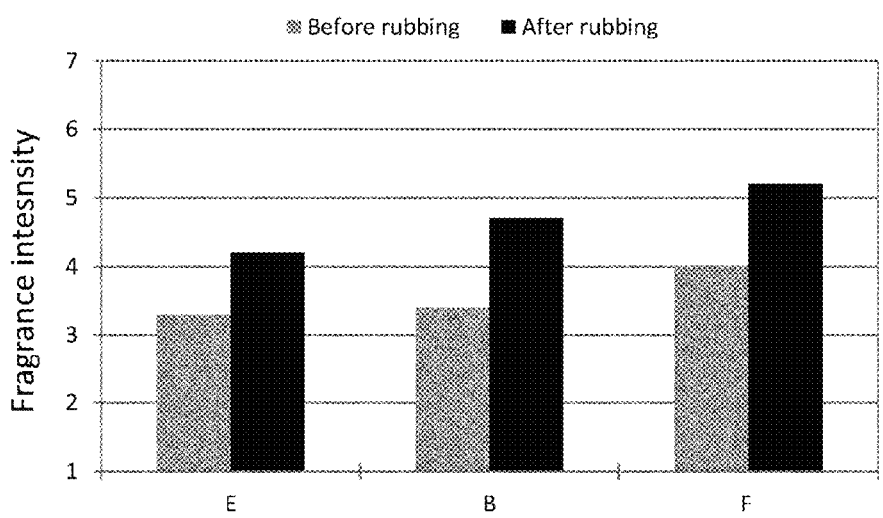
FIG. 4 represents olfactive performance of microcapsules according to the invention in a fabric softener.
Figure 5:
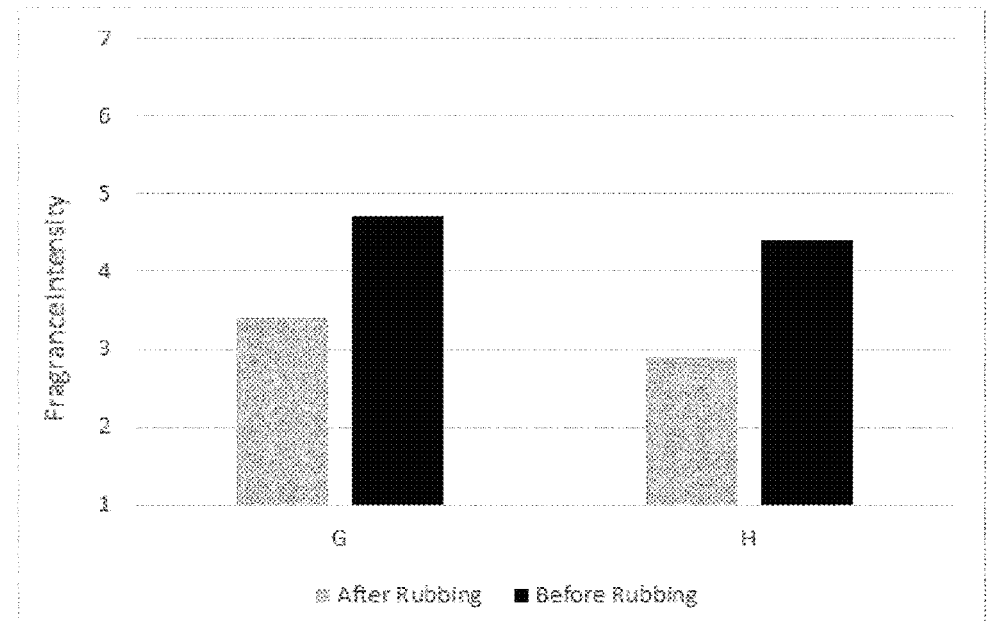
FIG. 5 represents olfactive performance of microcapsules according to the invention in a fabric softener.

As it can be seen from FIGS. 3, 4 and 5, the microcapsules of the invention demonstrate a significant burst effect after rubbing.

Example 5

Olfactive Performance in a Liquid Detergent Composition

The olfactive performance of the microcapsule of the invention was studied in a liquid detergent base.

Microcapsule slurry B of the present invention was dispersed in liquid detergent base described in table 6 to obtain a concentration of encapsulated perfume oil at 0.22%.

TABLE 6

Composition of the liquid detergent formulation

| Ingredients | Concentration [wt %] |
|---|---|
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Protease | 0.2 |
| Amylase | 0.2 |
| Mannanase | 0.2 |
| Acrylates/Steareth-20 Methacrylate structuring Crosspolymer[4] | 6 |
| Deionized Water | 27.4 |

[1]Hostapur SAS 60; Origin: Clariant
[2]Edenor K 12-18; Origin: Cognis
[3]Genapol LA 070; Origin: Clariant
[4]Aculyn 88; Origin: Dow Chemical a. Protocol Fabrics (2.0 kg of cotton terry towels) were washed with 35 g of liquid detergent containing 0.15% encapsulated oil (perfume A) at 40° C. in a standard European horizontal axis machine (Miele Novotronic W 900-79 CH).

The liquid detergent was placed in the drum of the washing machine at the start of the wash. After the wash, fabrics were line-dried overnight before the odor intensity of the cotton towels was evaluated by an expert panel of 10 trained panelists. The panelists were asked to rate the odor intensity of the towels on a scale from 1 to 7, 1 corresponding to odorless and 7 corresponding to a very strong odor.

b. Results

Figure 6:
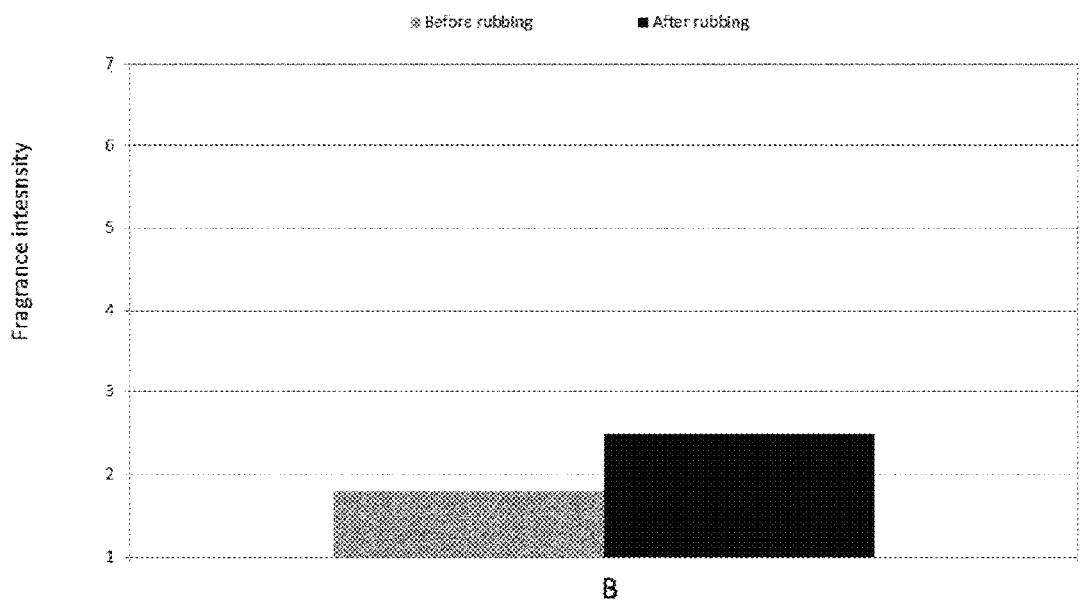
FIG. 6 represents olfactive performance of microcapsules according to the invention in a liquid detergent.

The results are shown in FIG. 6.

c. Conclusions

The microcapsule of the invention demonstrate a clear and significant burst effect after rubbing (test=0.011).

Example 6

Olfactive Performance in a Rinse-Off Conditioner

Microcapsule slurry B was incorporated at the required dosage (corresponding to an encapsulated perfume oil at 0.5%) in the rinse-off base (see Table 6) with sample stirring at room temperature.

10 g Caucasian brown hair swatches were used with a length of 20 cm and fixed with a flat metal clip. Caucasian hair, flat bundled, was chosen for this evaluation because Caucasian hair is rather thin in diameter and the application of viscous conditioner compositions can be guaranteed to be more reproducible compared to thick and course Asian hair. The hair swatches were rinsed with warm tap water (37° C.) and excess water was squeezed off manually. 1 g of the rinse-off product was applied on the swatch and distributed manually during 30 seconds, wearing nitrile gloves. Swatches were then air dried on a drying rack during 24 hours. Olfactive evaluation was carried out by a group of 8 panelists on the dried swatches before and after combing. The intensity was reported on a scale from 1-7 (1=no odor, 7=maximum odor intensity). The average of 8 panelist evaluations is reported.

TABLE 7 rinse-off conditioner composition

| Ingredients | Concentration [wt %] |
|---|---|
| A Water deionized | 81.8 |
| Behentrimonium Chloride [1] | 2.5 |
| Hydroxyethylcellulose [2] | 1.5 |
| B Cetearyl Alcohol [3] | 4 |
| Glyceryl Stearate (and) PEG-100 Stearate [4] | 2 |
| Behentrimonium Methosulfate (and) Cetyl alcohol (and) Butylene Glycol [5] | 4 |
| Ethoxy (20) Stearyl Alcohol [6] | 1 |

TABLE 7-continued rinse-off conditioner composition

| Ingredients | Concentration [wt %] |
|---|---|
| C Amodimethicone (and) Trideceth-12 (and) Cetrimonium Chloride [7] | 3 |
| Chlorhexidine Digluconate [8] 20% aqueous solution | 0.2 |
| D Citric acid 10% aqueous sol. till pH 3.5-4 | q.s. |
| TOTAL: | 100 |

[1] Genamin KDM P, Clariant
[2] Tylose H10 Y G4, Shin Etsu
[3] Lanette O, BASF
[4] Arlacel 165-FP-MBAL-PA-(RB), Croda
[5] Incroquat Behenyl TMS-50-MBAL-PA-(MH) HA4112, Croda
[6] SP Brij S20 MBAL-PA(RB), Croda
[7] Xiameter DC MEM-0949 Emulsion, Dow Corning
[8] Alfa Aesar Ingredients of Phase A are mixed until a uniform mixture was obtained. Tylose is allowed to completely dissolve. Then the mixture is heated up to 70-75° C. Ingredients of Phase B are combined and melted at 70-75° C. Then ingredients of Phase B are added to Phase A with good agitation and the mixing is continued until cooled down to 60° C. Then, ingredients of Phase C are added while agitating and keeping mixing until the mixture cooled down to 40° C. The pH is adjusted with citric acid solution till pH: 3.5-4.0.

Figure 7:
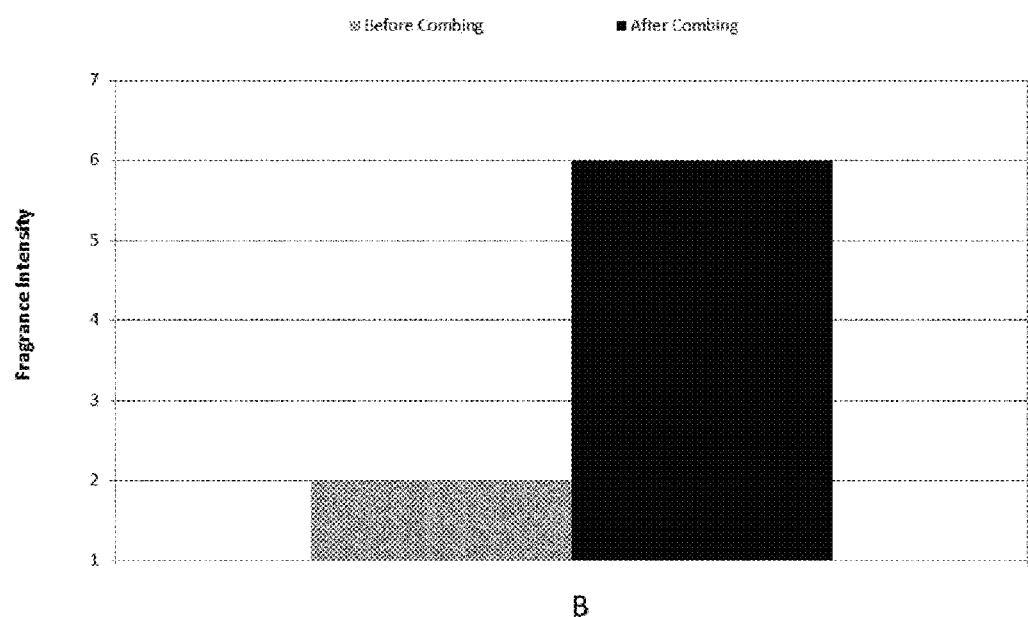
FIG. 7 represents olfactive performance of microcapsules according to the invention in a rinse-off conditioner.

One can note from FIG. 7 that microcapsules, according to the invention, show a combing effect.

Example 7

Spray-Dried Microcapsules Preparation

Emulsions 1-5 having the following ingredients are prepared.

TABLE 8

Composition of Emulsions 1-5 and composition of granulated powder 1-5 after spray-drying

| Ingredients | Emulsion 1 | Emulsion 2 | Emulsion 3 | Emulsion 4 | Emulsion 5 |
|---|---|---|---|---|---|
| Modified starch [1] | 2.6% | 2.6% | 2.6% | 12.5% | 2% |
| Maltodextrin [2] | 26.8% | 22.8% | 19.3% | 0% | 19.1% |
| Maltose [3] | 0% | 0% | 0% | 7.9% | 0% |
| Citric Acid | 0% | 0% | 0% | 1% | 0% |
| Tripotassium Citrate | 0% | 0% | 0% | 1.9% | 0% |
| Microcapsules (B, G or H) | 12.0% | 24% | 37.0% | 8.9% | 56.2% |
| Silica [4] | 1.1% | 1.1% | 1.1% | 0% | 0% |
| Free Perfume C [5] | 0% | 0% | 0% | 11% | 0% |
| Water | 57.6% | 49.6% | 40.1% | 56.9% | 22.7% |

| | Granule 1 | Granule 2 | Granule 3 | Granule 4 | Granule 5 |
|---|---|---|---|---|---|
| Modified starch [1] | 7.5% | 7.4% | 7.2% | 31.6% | 4.9% |
| Maltodextrin [2] | 77.4% | 65.5% | 53.8% | 0% | 44.7% |
| Maltose | 0% | 0% | 0% | 20.9% | |
| Citric Acid | 0% | 0% | 0% | 2.6% | 0% |
| Tripotassium citrate | 0% | 0% | 0% | 4.9% | 0% |
| Encapsulated perfume C | 0% | 0% | 0% | 28.1% | 0% |
| Microcapsules (B, G or H) | 12.% | 24.1% | 36.1% | 9.8% | 48.4% |

TABLE 8-continued

| Composition of Emulsions 1-5 and composition of granulated powder 1-5 after spray-drying | | | | | |
|---|---|---|---|---|---|
| Silica | 3.0 | 3.0% | 2.9% | 2.0% | 2% |
| Fragrance loading in powder after spray-drying | 10.1% | 20.1% | 30% | 35.8% | 40.2% |

[1] CapsulTM, Ingredion
[2] Maltodextrin 10DE origin: Roquette
[3] Maltose, Lehmann & Voss
[4] Silica, Evonik
[5] see table 9

TABLE 9

| Composition of Perfume C | |
|---|---|
| Component | % |
| ACETATE DE 4-(1,1-DIMETHYLETHYL)-1-CYCLOHEXYLE [1] | 14.50 |
| LINALOL | 10.50 |
| 3-(4-TERT-BUTYLPHENYL)-2-METHYLPROPANAL [2] | 10.00 |
| 1-(OCTAHYDRO-2,3,8,8-TETRAMETHYL-2-NAPHTALENYL)-1-ETHANONE [3] | 10.00 |
| CITRONELLYL NITRILE | 9.00 |
| DIPHENYLOXYDE | 6.50 |
| ISOBORNYL ACETATE | 6.00 |
| BETA IONONE | 6.00 |
| TRICYCLO[5.2.1.0~2,6~]DEC-3-EN-8-YL ACETATE (A) + TRICYCLO[5.2.1.0~2,6~]DEC-4-EN-8-YL ACETATE (B) [4] | 5.50 |
| ETHER MT | 4.00 |
| METHYL DIHYDROJASMONATE [5] | 4.00 |
| GERANIOL 60 | 3.00 |
| CITRAL | 2.50 |
| ALDEHYDE C 10 | 2.50 |
| ALLYL HEPTANOATE | 2.50 |
| ETHYL METHYL-2-BUTYRATE | 1.50 |
| GERANYL ACETATE | 1.00 |
| 2,4-DIMETHYL-3-CYCLOHEXENE-1-CARBALDEHYDE [6] | 1.00 |

[1] Firmenich SA, Switzerland
[2] Givaudan SA, Vernier, Switzerland
[3] International Flavors & Fragrances, USA
[4] Firmenich SA, Switzerland
[5] Firmenich SA, Switzerland
[6] Firmenich SA, Switzerland Components for the polymeric matrix (Maltodextrin and Capsul™, or Capsul™, citric acid and tripotassium citrate) are added in water at 45-50° C. until complete dissolution.

For emulsion 4, free perfume C is added to the aqueous phase.

Microcapsules slurry is added to the obtained mixture. Then, the resulting mixture is then mixed gently at 25° C. (room temperature).

Granulated powder 1-5 are prepared by spray-drying Emulsion A-E using a Sodeva Spray Dryer (Origin France), with an air inlet temperature set to 215° C. and a throughput set to 500 ml per hour. The air outlet temperature is of 105° C. The emulsion before atomization is at ambient temperature.

Example 8

Liquid Scent Booster Composition

A sufficient amount of a microcapsule slurry (A-O) is weighed and mixed in a liquid scent booster to add the equivalent of 0.2% perfume.

Different ringing gel compositions are prepared (compositions 1-6) according to the following protocol.

TABLE 10

| Liquid scent booster composition | | | | | | |
|---|---|---|---|---|---|---|
| | Amount (% wt) | | | | | |
| Ingredients | 1 | 2 | 3 | 4 | 5 | 6 |
| Water | 71.20% | 89.5% | 78.8% | 79.4% | 70% | 70% |
| Propylene glycol | 20.30% | — | — | — | 20% | 20% |
| Polyethylene glycol ethers of decyl alcohol[1] | 4.00% | 6% | | | | |
| Polyethylene glycol ether of Lauryl Alcohol[2] | | | | | 4.00% | 4.00% |
| alkyl polyglucoside C8-C10[3] | | | 8.30% | 7.7% | | |
| Deceth-3[1] | 1.50% | | | | | |
| Lauryl lactate | | | | 1% | | |
| Lauric acid | | 1.5% | 1.60% | | | |
| Glyceryl Caprylate | | | | | 3.00% | 3.00% |
| Fragrance | 3.00% | 3.0% | 3.00% | 3.00% | 3.00% | 0% |

[1] Deceth-8; trademark and origin: KLK Oleo
[2] Laureth-9; ; trademark and origin
[3] Plantacare 2000UP; trademark and origin: BASF In a first step, the aqueous phase (water), the solvent (propylene glycol) if present and surfactants are mixed together at room temperature under agitation with magnetic stirrer at 300 rpm for 5 min.

In a second step, the linker is dissolved in the hydrophobic active ingredient (fragrance) at room temperature under agitation with magnetic stirrer at 300 rpm. The resulting mixture is mixed for 5 min.

Then, the aqueous phase and the oil phase are mixed together at room temperature for 5 min leading to the formation of a transparent or opalescent ringing gel.

Example 9

Powder Detergent Composition

A sufficient amount of granules 1-5 is weighed and mixed in a powder detergent composition to add the equivalent of 0.2% perfume.

TABLE 11

Powder detergent composition

| Ingredients | Part |
| --- | --- |
| Anionic (Linear Alkyl Benzene Sulphonates) | 20% |
| Nonionics (Alcohol Ethoxylates (5-9 ethylene oxide) | 6% |
| Builders (zeolites, sodium carbonate) | 25% |
| Silicates | 6% |
| Sodium Sulphate | 35% |
| Others (Enzymes, Polymers, Bleach) | 7.5% |
| Spray-dried granule powder 1-5 | 0.5% |

Example 10

Concentrated all Purpose Cleaner Composition

A sufficient amount of microcapsule slurry B, F, H, I or J is weighed and mixed in a concentrated all-purpose cleaner composition to add the equivalent of 0.2% perfume.

TABLE 12 concentrated all-purpose cleaner composition

| Ingredients | Amount (% wt) | Function |
| --- | --- | --- |
| Ethoxylated Alcohol (C9-C11, 8EO) [1] | 20 | Non-ionic surfactant |
| Sodium Dodecyl Benzene Sulfonate [2] | 16 | Anionic surfactant |
| Sodium Cumene Sulfonate [3] | 8 | Hydrotrope |
| Methyl chloro isothiazolinone Methyl isothiazolinone 3.3:1 [4] | 0.8% | preservative |
| Water | 55.9 | solvent |

[1] Neodol 91-8 ®; trademark and origin: Shell Chemical
[2] Biosoft D-40 ®; trademark and origin: Stepan Company
[3] Stepanate SCS ®; trademark and origin: Stepan Company
[4] Kathon CG ®; trademark and origin: Dow Chemical Company All ingredients are mixed together and then the mixture was diluted with water to 100%.

Example 11

Solid Scent Booster Composition

A sufficient amount of microcapsules in dried form is weighed and mixed with a solid scent booster composition to add the equivalent of 0.2% perfume.

TABLE 13

Salt-based solid scent booster compositions

| Ingredients | Part |
| --- | --- |
| Sodium chloride | 95 |
| Spray-dried granule powder 1-5 | 5 |

TABLE 14

Urea-based solid scent booster compositions

| Ingredients | Part |
| --- | --- |
| Urea (beads) | 94 |
| Spray-dried granule powder 1-5 | 8 |
| Bentonite | 3 |
| Perfume | 3 |

Example 12

Shampoo Composition

A sufficient amount of a microcapsule slurry (A-O) is weighed and mixed in a shampoo composition to add the equivalent of 0.2% perfume.

TABLE 15

Shampoo composition

| | Ingredients | Concentration [wt %] |
| --- | --- | --- |
| A | Water deionized | 44.4 |
| | Polyquaternium-10 [1] | 0.3 |
| | Glycerin 85% [2] | 1 |
| | DMDM Hydantoin [3] | 0.2 |
| B | Sodium Laureth Sulfate [4] | 28 |
| | Cocamidopropyl Betaine [5] | 3.2 |
| | Disodium Cocoamphodiacetate [6] | 4 |
| | Ethoxy (20) Stearyl Alcohol [6] | 1 |
| C | Sodium Laureth Sulfate [4] | 3 |
| | Glyceryl Laureate [7] | 0.2 |
| D | Water deionized | 1 |
| | Sodium Methylparaben [8] | 0.1 |
| E | Sodium Chloride 10% aqueous sol. | 15 |
| | Citric acid 10% aqueous sol. till pH 5.5-6 | q.s. |
| | Perfume | 0.5 |
| | TOTAL: | 100 |

[1] Ucare Polymer JR-400, Noveon
[2] Schweizerhall
[3] Glydant, Lonza
[4] Texapon NSO IS, Cognis
[5] Tego Betain F 50, Evonik
[6] Amphotensid GB 2009, Zschimmer & Schwarz
[7] Monomuls 90 L-12, Gruenau
[8] Nipagin Monosodium, NIPA Polyquaternium-10 is dispersed in water. The remaining ingredients of phase A are mixed separately by addition of one after the other while mixing well after each adjunction. Then this pre-mix is added to the Polyquaternium-1 dispersion and was mixed for 5 mi. Then Phase B and the premixed Phase C (heat to melt Monomuls 90L-12 in Texapon NSO IS) are added. The mixture is mixed well. Then, Phase D and Phase E are added while agitating. The pH was adjusted with citric acid solution till pH: 5.5-6.0.

Example 13

Shampoo Composition

A sufficient amount of a microcapsule slurry (A-O) is weighed and mixed in a shampoo composition to add the equivalent of 0.200 perfume.

TABLE 16

Shampoo composition

| | Ingredients | Concentration [wt %] |
|---|---|---|
| A | Water deionized | 45.97 |
| | Tetrasodium EDTA [1] | 0.05 |
| | Guar Hydroxypropyltrimonium Chloride [2] | 0.05 |
| | Polyquaternium-10 [3] | 0.075 |
| B | NaOH 10% aqueous sol. | 0.3 |
| C | Ammonium Lauryl Sulfate [4] | 34 |
| | Ammonium Laureth Sulfate [5] | 9.25 |
| | Cocamidopropyl Betaine [6] | 2 |
| | Dimethicone (&) C12-13 Pareth-4 (&) C12-13 Pareth-23 (&) Salicylic Acid [7] | 2.5 |
| D | Cetyl Alcohol [8] | 1.2 |
| | Cocamide MEA [9] | 1.5 |
| | Glycol Distearate [10] | 2 |
| E | Methylchloroisothiazolinone & Methylisothiazolinone [11] | 0.1 |
| | D-Panthenol 75% [12] | 0.1 |
| | Water deionized | 0.3 |
| F | Sodium Chloride 25% aqueous sol. | 0.6 |
| | TOTAL: | 100 |

[1] EDETA B Powder, BASF
[2] Jaguar C14 S, Rhodia
[3] Ucare Polymer JR-400, Noveon
[4] Sulfetal LA B-E, Zschimmer & Schwarz
[5] Zetesol LA, Zschimmer & Schwarz
[6] Tego Betain F 50, Evonik
[7] Xiameter MEM-1691, Dow Corning
[8] Lanette 16, BASF
[9] Comperlan 100, Cognis
[10] Cutina AGS, Cognis
[11] Kathon CG, Rohm & Haas
[12] D-Panthenol, Roche A premix comprising Guar Hydroxypropyltrimonium Chloride and Polyquaternium-10 are added to water and Tetrasodium EDTA while mixing. When the mixture is homogeneous, NaOH is added. Then, Phase C ingredients are added and the mixture was heat to 75° C. Phase D ingredients are added and mixed till homogeneous. The heating is stopped and temperature of the mixture is decreased to RT. At 45° C., ingredients of Phase E while mixing final viscosity is adjusted with 25% NaCl solution and pH of 5.5-6 is adjusted with 10% NaOH solution.

Example 14

Antiperspirant Spray Anhydrous Composition

A sufficient amount of a microcapsule slurry (A-O) is weighed and mixed in an antiperspirant spray anhydrous composition to add the equivalent of 0.2% perfume.

TABLE 17 antiperspirant spray anhydrous composition

| Ingredient | Amount (wt %) |
|---|---|
| Cyclomethicone[1] | 53.51 |
| Isopropyl miristate | 9.04 |
| Silica[2] | 1.03 |
| Quaternium-18-Hectorite[3] | 3.36 |
| Aluminium Chlorohydrate[4] | 33.06 |

[1] Dow Corning ® 345 Fluid; trademark and origin: Dow Corning
[2] Aerosil ® 200; trademark and origin: Evonik
[3] Bentone ® 38; trademark and origin: Elementis Specialities
[4] Micro Dry Ultrafine; origin: Reheis Using a high speed stirrer, Silica and Quaternium-18-Hectorite are added to the Isopropyl miristate and Cyclomethicone mixture. Once completely swollen, Aluminium Chlorohydrate is added portion wise under stirring until the mixture was homogeneous and without lumps. The aerosol cans are filled with 25% Suspension of the suspension and 75% of Propane/Butane (2.5 bar).

Example 15

Antiperspirant Spray Emulsion Composition

A sufficient amount of a microcapsule slurry (A-O) is weighed and mixed in antiperspirant spray emulsion composition to add the equivalent of 0.2% perfume.

TABLE 18 antiperspirant spray emulsion composition

| Ingredient | Amount (wt %) |
|---|---|
| Polysorbate 65[1] (Part A) | 0.95 |
| Polyglyceryl-2 dipolyhydroxystearate[2] (Part A) | 1.05 |
| Cetyl PEG/PPG-10/1 Dimethicone[3] (Part A) | 2.75 |
| Cyclomethicone[4] (Part A) | 16.4 |
| Isopropylisostearate[5] (Part A) | 4.5 |
| Phenoxyethanol[6] (Part A) | 0.5 |
| Ethylhexylglycerin[7] (Part A) | 0.2 |
| C12-15 Alkyl Benzoate[8] (Part A) | 5.65 |
| Silica Silylate[9] (Part A) | 0.1 |
| Sodium Methylparaben[10] (Part B) | 0.1 |
| Aluminium Chlorohydrate[11] (Part B) | 20 |
| Water (Part B) | 44.47 |
| Fragrance (Part C) | 3.33 |

[1] Tween 65; trademark and origin: CRODA
[2] Dehymuls PGPH; trademark and origin: BASF
[3] Abil EM-90; trademark and origin: BASF
[4] Dow Corning 345 fluid; trademark and origin: Dow Corning
[5] Crodamol ipis; trademark and origin: CRODA
[6] Phenoxyethanol; trademark and origin: LANXESS
[7] Sensiva sc 50; trademark and origin: KRAFT
[8] Tegosoft TN; trademark and origin: Evonik
[9] Aerosil R 812; trademark and origin: Evonik
[10] Nipagin mna; trademark and origin: CLARIANT
[11] Locron L; trademark and origin: CLARIANT The ingredients of Part A and Part B are weighted separately. Ingredients of Part A are heated up to 60° C. and ingredients of Part B are heated to 55° C. Ingredients of Part B are poured small parts while continuous stirring into A. Mixture were stirred well until the room temperature was reached. Then, ingredients of part C are added. The emulsion is mixed and is introduced into the aerosol cans. The propellant is crimped and added.

Aerosol filling: 30% Emulsion: 70% Propane/Butane 2.5 bar

Example 16

Deodorant Spray Composition

A sufficient amount of a microcapsule slurry (A-O) is weighed and mixed in antiperspirant deodorant spray composition to add the equivalent of 0.2% perfume.

TABLE 19 deodorant spray composition

| Ingredient | Amount (wt %) |
| --- | --- |
| Ethanol 95% | 90.65 |
| Triclosan[1] | 0.26 |
| Isopropyl miristate | 9.09 |

[1]Irgasan ® DP 300; trademark and origin: BASF

All the ingredients according to the sequence of the Table above are mixed and dissolved. Then the aerosol cans are filled, crimp and the propellant is added (Aerosol filling: 40% active solution 60% Propane/Butane 2.5 bar).

Example 17

Antiperspirant Roll-on Emulsion Composition

A sufficient amount of a microcapsule slurry (A-O) is weighed and mixed in antiperspirant roll-on emulsion composition to add the equivalent of 0.2% perfume.

TABLE 20 antiperspirant roll-on emulsion composition

| Ingredient | Amount (wt %) |
| --- | --- |
| Steareth-2[1] (Part A) | 3.25 |
| Steareth-21[2] (Part A) | 0.75 |
| PPG-15 Stearyl Ether[3] (Part A) | 4 |
| WATER deionised (Part B) | 51 |
| Aluminum Chlorohydrate 50% aqueous solution[4] (Part C) | 40 |
| Fragrance (Part D) | 1 |

[1]BRIJ 72; origin: ICI
[2]BRIJ 721; origin: ICI
[3]ARLAMOL E; origin: UNIQEMA-CRODA
[4]LOCRON L; origin: CLARIAN Part A and B are heated separately to 75° C.; Part A is added to part B under stirring and the mixture is homogenized for 10 minutes. Then, the mixture is cooled down under stirring; and part C is slowly added when the mixture reached 45° C. and part D when the mixture reached at 35° C. while stirring. Then the mixture is cooled down to RT.

Example 18

Antiperspirant Roll-on Composition

A sufficient amount of a microcapsule slurry (A-O) is weighed and mixed in antiperspirant roll-on composition to add the equivalent of 0.2% perfume.

TABLE 21 antiperspirant roll-on composition

| Ingredient | QUANTITY |
| --- | --- |
| Water (Part A) | 45 |
| Aluminum Chlorohydrate 50% aqueous solution[1] (Part B) | 20 |
| Alcohol Denat. (Ethanol 96%) (Part B) | 30 |
| Ceteareth-12[2] (Part C) | 2 |
| Ceteareth-30[3] (Part C) | 2 |
| Fragrance (Part D) | 1 |

[1]LOCRON L; origin: CLARIANT
[2]EUMULGIN B-1; origin: BASF
[3]EUMULGIN B-3; origin: BASF The ingredients of part B are mixed in the vessel then ingredient of part A is added. Then dissolved part C in part A and B. With perfume, 1 part of Cremophor RH40 for 1 part of perfume is added while mixing well

Example 19

Antiperspirant Roll-on Composition

A sufficient amount of a microcapsule slurry (A-O) is weighed and mixed in antiperspirant roll-on emulsion composition to add the equivalent of 0.2% perfume.

TABLE 22 antiperspirant roll-on emulsion composition

| Ingredient | Amount (wt %) |
| --- | --- |
| Water (Part A) | 50.51 |
| Hydroxyethylcellulose[1] (Part A) | 0.71 |
| Ethanol 95% (Part B) | 40.40 |
| 1,2-Propylene Glycol (Part B) | 5.05 |
| Triclosan[2] (Part B) | 0.30 |
| PEG-40 Hydrogenated castor oil[3] (Part C) | 3.03 |

[1]Natrosol ® 250 H; trademark and origin: Ashland
[2]Irgasan ® DP 300; trademark and origin: BASF
[3]Cremophor ® RH 40; trademark and origin: BASF Part A is prepared by sprinkling little by little the Hydroxyethylcellulose in the water whilst rapidly stirring with the turbine. Stirring is continued until the Hydroxyethylcellulose is entirely swollen and giving a limpid gel. Then, Part B is poured little by little in Part A whilst continuing stirring until the whole is homogeneous. Part C is added.

Example 20

Deodorant Pump without Alcohol Formulation

A sufficient amount of a microcapsule slurry (A-O) is weighed and mixed in the following composition to add the equivalent of 0.2% perfume.

TABLE 23 deodorant composition

| Ingredients | Amount (wt %) |
| --- | --- |
| C12-15 Alkyl Lactate[1] | 5 |
| Dimethicone[2] | 91.6 |
| Cetyl Lactate[3] | 1 |
| Octyl dodecanol[4] | 0.8 |

TABLE 23-continued deodorant composition

| Ingredients | Amount (wt %) |
|---|---|
| Triclosan[5] | 0.1 |
| PERFUME | 1.5 |

[1]Ceraphyl 41; trademark and origin ASHLAND
[2]DOW CORNING 200 FLUID 0.65 cs; trademark and origin DOW CORNING CORPORATION
[3]Ceraphyl 28; trademark and origin ASHLAND
[4]Eutanol G; trademark and origin BASF
[5]Irgasan ® DP 300; trademark and origin: BASF All the ingredients are mixed according to the sequence of the table and the mixture is heated slightly to dissolve the Cetyl Lactate.

Example 21

Deodorant Pump with Alcohol Formulation

A sufficient amount of a microcapsule slurry (A-O) is weighed and mixed in the following composition to add the equivalent of 0.2% perfume.

TABLE 24 deodorant composition

| Ingredients | Amount (wt %) |
|---|---|
| Ethyl Alcohol (Part A) | 60 |
| PEG-6 Caprylic/Capric Glycerides[1] (Part A) | 2 |
| Water (Part A) | 35.6 |
| PEG-40 Hydrogenated Castor Oil[2] (Part B) | 0.4 |
| PERFUME (Part B) | 2 |

[1]Softigen 767; trademark and origin CRODA
[2]Cremophor ® RH 40; trademark and origin: BASF Ingredients from Part B are mixed together. Ingredients of Part A are dissolved according to the sequence of the Table and are poured into part B.

Example 22

Deodorant Stick without Alcohol Formulation

A sufficient amount of a microcapsule slurry (A-O) is weighed and mixed in the following composition to add the equivalent of 0.2% perfume.

TABLE 25 deodorant composition

| Ingredient | Amount (wt %) |
|---|---|
| Stearic acid (Part A) | 5.05 |
| 1,2-propylene glycol (Part A) | 41.87 |
| Sodium hydroxide 20% aqueous solution (Part A) | 4.24 |
| Water (Part A) | 30.30 |
| Tetrasodium EDTA[1] (Part A) | 0.10 |
| Ceteareth-25[2] (Part A) | 1.52 |
| PPG-3 Myristyl ether[3] (Part A) | 1.52 |

TABLE 25-continued deodorant composition

| Ingredient | Amount (wt %) |
|---|---|
| 1,2-propylene glycol (Part B) | 15.14 |
| Triclosan[4] (Part B) | 0.25 |

[1]Edeta ® B Power; trademark and origin: BASF
[2]Cremophor ® A25; trademark and origin: BASF
[3]Tegosoft ® APM; trademark and origin: Evonik
[4]Irgasan ® DP 300; trademark and origin: BASF All the components of Part A are weighted and heated up to 70-75° C. Ceteareth-25 is added once the other Part A ingredients are mixed and heated. Once the Ceteareth-25 is dissolved, the Stearic Acid is added. Part B is prepared by dissolving the Triclosan in 1,2 Propylene Glycol. Water which has evaporated is added. Slowly under mixing, Part B is poured into part A. To stock, a plastic bag into the bucket is put in to be sealed after cooling. Moulds was filled at about 70° C.

Example 23

Anti-Perspirant Stick

A sufficient amount of a microcapsule slurry (A-O) is weighed and mixed in the following composition to add the equivalent of 0.2% perfume.

TABLE 26 deodorant composition

| Ingredient | Amount (wt %) |
|---|---|
| Cyclomethicone[1] (Part A) | 55.56 |
| Stearyl Alcohol[2] (Part A) | 21.21 |
| PPG-14 Butyl ether[3] (Part A) | 2.02 |
| Hydrogenated Castor Oil[4] (Part A) | 1.01 |
| Aluminium Zirconium tetrachlorohydrex-Gly[5] (Part B) | 20.20 |

[1]Dow Corning ® 345 Fluid; trademark and origin: Dow Corning
[2]Lanette ® 18; trademark and origin: BASF
[3]Tegosoft ® PBE; trademark and origin: Evonik
[4]Cutina ® HR; trademark and origin: BASF
[5]Summit AZP-908; trademark and origin: Reheis All the components of Part A are weighted, heated up to 70-75° C. and mixed well. Ingredient of Part B is dispersed in Part A. The mixture is mixed and putted into a tick at 65° C.

Example 24

Day Cream

A sufficient amount of a microcapsule slurry (A-O) is weighed and mixed in the following composition to add the equivalent of 0.2% perfume.

TABLE 27 day cream

| Ingredients | % |
|---|---|
| ARLATONE 985 Ethoxylated Fatty Alcohol Ester | 5.000 |
| CETYL ALCOHOL | 0.500 |
| TEFOSE 2561 Ceteth-20 (and) Glyceryl Stearate (and) PEG-6 Stearate (and) Steareth-20 | 4.000 |

TABLE 27-continued day cream

| Ingredients | % |
|---|---|
| COSBIOL | 1.000 |
| Squalan | |
| MINERAL OIL 30-40 cp | 2.000 |
| Paraffin Oil | |
| PETROLEUM JELLY | 6.000 |
| Petrolatum | |
| WATER deionized | 75.850 |
| PROPYLENE GLYCOL | 5.000 |
| GLYDANT PLUS | 0.150 |
| DMDM Hydantoin (and) Iodopropynyl Butylcarbamate | |
| PNC 400 | 0.200 |
| Sodium Carbomer | |
| PERFUME | 0.300 |
| Total | 100.00 |

Example 25

Talc Formulation

A sufficient amount of granules 1-5 is weighed and mixed in introduced in a standard talc base: 100% talc, very slight characteristic odor, white powder, origin: LUZENAC to add the equivalent of 0.2% perfume.

Example 26

Shower-gel composition A sufficient amount of a microcapsule slurry (A-O) is weighed and mixed in the following composition to add the equivalent of 0.2% perfume.

TABLE 28 shower gel composition

| Ingredients | Amount (% wt) | Function |
|---|---|---|
| WATER deionised | 49.350 | Solvent |
| Tetrasodium EDTA [1] | 0.050 | Chelating agent |
| Acrylates Copolymer[2] | 6.000 | Thickener |
| Sodium C12-C15 Pareth Sulfate [3] | 35.000 | Surfactant |
| Sodium Hydroxide 20% aqueous solution | 1.000 | pH adjuster |
| Cocamidopropyl Betaine[4] | 8.000 | Surfactant |
| Methylchloroisothiazolinone and Methylisothiazolinone[5] | 0.100 | Preservative |
| Citric Acid (40%) | 0.500 | pH adjuster |

7) EDETA B POWDER; trademark and origin: BASF
8) CARBOPOL AQUA SF-1 POLYMER; trademark and origin: NOVEON
9) ZETESOL AO 328 U; trademark and origin: ZSCHIMMER & SCHWARZ
10) TEGO-BETAIN F 50; trademark and origin: GOLDSCHMIDT
11) KATHON CG; trademark and origin: ROHM & HASS Ingredients are mixed, pH is adjusted to 6-6.3 (Viscosity: 4500 cPo+/−1500 cPo (Brookfield RV/Spindle #4/20 RPM)).

Example 27

Shower-Gel Composition

A sufficient amount of a microcapsule slurry (A-O) is weighed and mixed in the following composition to add the equivalent of 0.2% perfume.

TABLE 29 shower gel composition

| Ingredients | Amount (% wt) | Function |
|---|---|---|
| WATER deionized | 52.40 | Solvent |
| Tetrasodium EDTA [1] | 0.10 | Chelating agent |
| Sodium Benzoate | 0.50 | Preservative |
| Propylene Glycol | 2.00 | Solvent |
| Sodium C12-C15 Pareth Sulfate [2] | 35.00 | Surfactant |
| Cocamidopropyl Betaine[3] | 8.00 | Surfactant |
| Polyquaternium-7[4] | 0.20 | Conditioning agent |
| Citric Acid (40%) | 1.00 | pH adjuster |
| Sodium Chloride | 0.80 | Viscosity adjuster |

[1] EDETA B POWDER; trademark and origin: BASF
[2] ZETESOL AO 328 U; trademark and origin: ZSCHIMMER & SCHWARZ
[3] TEGO-BETAIN F 50; trademark and origin: GOLDSCHMIDT
[4] MERQUAT 550; trademark and origin: LUBRIZOL Ingredients are mixed, pH is adjusted to 4.5 (Viscosity: 3000 cPo+/−1500 cPo (Brookfield RV/Spindle #4/20 RPM)).

Example 28

Shower-Gel Composition

A sufficient amount of a microcapsule slurry (A-O) is weighed and mixed in the following composition to add the equivalent of 0.2% perfume.

TABLE 30 shower gel composition

| Ingredients | Amount (% wt) | Function |
|---|---|---|
| WATER deionized | 50.950 | Solvent |
| Tetrasodium EDTA [1] | 0.050 | Chelating agent |
| Sodium Benzoate | 0.50 | Preservative |
| Glycerin 86% | 3.50 | Solvent |
| Sodium Laureth Sulfate [2] | 27.0 | Surfactant |
| Polyquaternium-7[3] | 1.0 | Conditioning Agent |
| Coco-Betaine[4] | 6.0 | Surfactant |
| PEG-120 Methyl Glucose trioleate[5] | 1.0 | Thickener |
| Citric Acid (40%) | 1.0 | pH adjuster |
| Glycol Distearate & Laureth-4 & Cocamidopropyl Betaine[6] | 3.0 | Pearlizing agent |
| Sodium Chloride 20% | 5.0 | Viscosity adjuster |
| PEG-40 Hydrogenated Castor Oil[7] | 1.0 | Viscosity adjuster |

[1] EDETA B POWDER; trademark and origin: BASF
[2] Texapon NSO IS; trademark and origin: COGNIS
[3] MERQUAT 550; trademark and origin: LUBRIZOL
[4] DEHYTON AB-30; trademark and origin: COGNIS
[5] GLUCAMATE LT; trademark and origin: LUBRIZOL
[6] EUPERLAN PK 3000 AM; trademark and origin: COGNIS
[7] CREMOPHOR RH 40; trademark and origin: BASF Ingredients are mixed, pH is adjusted to 4.5 (Viscosity: 4000 cPo+/−1500 cPo (Brookfield RV/Spindle #4/20 RPM))

Example 29

Hair Coloration Composition

A sufficient amount of a microcapsule slurry (A-O) is weighed and mixed with alkaline base A to add the equivalent of 0.20 perfume.

TABLE 31

Composition of the alkaline base A

| Ingredients | % |
|---|---|
| Phase A | |
| Water | 39.13 |
| Carbomer [1] | 0.9 |
| p-phenylenediamine [2] | 1 |
| m-aminophenol [3] | 1 |
| m-phenylenediamine sulfate [4] | 0.07 |
| resorcinol [5] | 0.5 |
| Phase B | |
| Propylene glycol | 6 |
| Laureth-2 [6] | 6 |
| Laureth-12 [7] | 6 |
| Dimethicone [8] | 0.7 |
| Phase C | |
| Cetearyl alcohol [9] | 18 |
| Oleth-30 [10] | 3 |
| Lauric acid | 3 |
| Glycol distearate [11] | 3 |
| Phase D | |
| Sodium metabisulfite [12] | 0.4 |
| Silica dimethyl silyate | 0.3 |
| Pentasodium pentetate [13] | 0.2 |
| Polyquaternium-22 [14] | 1 |
| Ammonium Hydroxide [15] | 9.3 |
| Perfume | 0.5 |

[1] Carbopol Ultrez 10 Polymer
[2] Covastyle PAP
[3] Covastyle MAP
[4] Covastyle MPDS
[5] Resorcine
[6] Lipocol L 12
[7] Arlypon F
[8] Dow Corning 200 Fluid 350
[9] Lanette O
[10] Eumulgin O 30
[11] Cutina AGS
[12] Covastyle MBS
[13] Dissolvine D-40
[14] Merquat 280
[15] Ammonium hydroxide 30% aqueous solution Procedure:

All ingredients of Phase A were mixed and heated until 75° C.

All ingredients of Phase B were combined and melt at 70-75° C.

Phase B was added to Phase A (both at 70-75° C.) with good agitation.

Phase C was added while mixing continued until cooled down to room temperature

At room temperature Phase D ingredients were added while mixing

Remaining ingredients of Phase C were added under stirring.

TABLE 32

Composition of the oxidative base B

| Ingredients | % |
|---|---|
| Phase A | |
| Water | 75 |
| Phase B | |
| Cetearyl alcohol and dicethyl phospahate and Cteteth-20 phosphate [1] | 3.5 |
| Mineral oil [2] | 3.5 |
| Cetyl acetate and acetylated lanolin alcohol [3] | 0.35 |
| Steareth-20 [4] | 0.35 |
| Phase C | |
| Hydrogen peroxide [5] | 17 |
| Perfume | 0.3 |

[1] Crodafos CS 20 Acid
[2] Paraffin Oil 30-40 cPs
[3] Acetulan
[4] Brij 78P
[5] Hydrogen Peroxide 35% aqueous solution Procedure:

All ingredients of Phase A were mixed and heated until 75° C.

All ingredients of Phase B were combined and melt at 70-75° C.

Phase B was added to Phase A (both at 70-75° C.) with good agitation and mixing continued until cooled down to room temperature At room temperature Phase C ingredients were added while mixing

Example 30

Hand Dishwash

A sufficient amount of a microcapsule slurry (A-O) is weighed and mixed in the following composition to add the equivalent of 0.2% perfume.

TABLE 33

Hand dishwash composition

| Ingredients | Amount (% wt) | Function |
|---|---|---|
| Linear alkylbenzene sulfonic acid [1] | 20 | Anionic surfactant |
| Diethanol amide [2] | 3.5 | Foam booster |
| Sodium Hydroxide (50%) [3] | 3.4 | pH Adjuster/neutralizer |
| Secondary alcohol ethoxolate [4] | 2.5 | Non-ionic surfactant |
| Sodium xylene sulfonate | 6.3 | Hydrotrope |
| Water | 64.3 | Solvent |

[1] Biosoft S-118 ®; trademark and origin: Stepan Company
[2] Ninol 40-CO ®; trademark and origin: Stepan Company
[3] Stepanate SXS ®; trademark and origin: Stepan Company
[4] Tergitol 15-S-9 ®; trademark and origin: Dow Chemical Company Water with sodium hydroxide and diethanolamide are mixed. LAS is added. After the LAS is neutralized, the remaining ingredients are added. The pH was Checked (=7-8) and adjusted if necessary.

Example 31

Toothpaste Formulation

A sufficient amount of microcapsule slurry R (corresponding to microcapsules B except that a flavor is encapsulated instead of a perfume) is weighed and mixed in the following composition to add the equivalent of 0.2% flavor.

TABLE 34

Toothpaste formulation

| Ingredients | Amount (% wt) |
|---|---|
| Polyethylene glycol 400 | 2.0% |
| Xanthan Gum | 0.60% |
| Sorbitol 70% Solution | 50.0% |
| Sodium Fluoride | 0.220% |
| Sodium Benzoate | 0.20% |
| Water | 15.230% |
| Hydrated Silica[1] | 22.0% |
| Hydrated Silica[2] | 7.0% |
| Titanium Dioxide CI77891 | 0.500% |
| Sodium Lauryl Sulfate | 1.250% |
| Flavor | 1.20% |
| TOTAL | 100% |

[1]Tixosil 73; trademark and origin:
[2]Tixosil 43; trademark and origin:

Example 32

Dicalcium Phosphate Based Toothpaste Formulation

A sufficient amount of microcapsule slurry R (corresponding to microcapsules B except that a flavor is encapsulated instead of a perfume) is weighed and mixed in the following composition to add the equivalent of 0.2% flavor.

TABLE 35

Toothpaste formulation

| Ingredients | Amount (% wt) |
|---|---|
| Sodium carboxymethyl cellulose | 1.20% |
| Flavor | 1.20% |
| DI/Purified Water | Q.S to Final Wt. |
| Sodium Lauryl Sulfate | 1.30% |
| Glycerine | 20.0% |
| Sodium Saccharin | 0.20% |
| Dicalcium phosphate dihydrate | 36.0% |
| Methylparaben | 0.200% |
| Silica[1] | 3.0% |
| TOTAL | 100% |

[1]Aerosil ®200; trademark and origin:

Example 33

Mouthwash Alcohol Free Formulation

A sufficient amount of microcapsule slurry R (corresponding to microcapsules B except that a flavor is encapsulated instead of a perfume) is weighed and mixed in the following composition to add the equivalent of 0.2% flavor.

TABLE 36

Mouthwash formulation

| Ingredients | Amount (% wt) |
|---|---|
| Propylene Glycol | 10.0% |
| Flavor | 0.240% |
| DI/Purified Water | Q.S to Final Wt. |
| Poloxamer 407 NF | 0.240% |
| Sodium Lauryl Sulfate | 0.040% |
| Sorbitol 70% Solution | 10.0% |
| Sodium Saccharin | 0.030% |

TABLE 36-continued

Mouthwash formulation

| Ingredients | Amount (% wt) |
|---|---|
| Glycerine | 3.0% |
| Sodium Benzoate | 0.10% |
| Sucralose | 0.020% |
| Benzoic Acid | 0.050% |
| TOTAL | 100% |

Example 34

Mouthwash Formulation

A sufficient amount of microcapsule slurry R (corresponding to microcapsules B except that a flavor is encapsulated instead of a perfume) is weighed and mixed in the following composition to add the equivalent of 0.20% flavor.

TABLE 37

Mouthwash formulation

| Ingredients | Amount (% wt) |
|---|---|
| Ethyl Alcohol 190 Proof | 15.00% |
| Flavor | 0.24% |
| DI/Purified Water | Q.S to Final Wt. |
| Poloxamer 407 NF | 0.24% |
| Sodium Lauryl Sulfate | 0.04% |
| Sorbitol 70% Solution | 10.00% |
| Sodium Saccharin | 0.03% |
| Glycerine | 3.00% |
| Sodium Benzoate | 0.10% |
| Sucralose | 0.02% |
| Benzoic Acid | 0.05% |
| TOTAL | 100% |

The invention claimed is:

1. A composite microcapsule slurry comprising at least one microcapsule having:
   an oil phase core comprising a hydrophobic material, and
   a composite shell comprising a first material and a second material, wherein:
      the first material and the second material are different,
      the first material is a coacervate,
      the second material is a polymeric material, and
      the weight ratio in the slurry between the first material and the second material is between 80:20 and 99.9:0.1;
   wherein the second material is present in an amount less than 1%, by weight based on the total weight of the microcapsule slurry.

2. The microcapsule slurry according to claim 1, wherein the second material is selected from the group consisting of polyurea, polyester, polyurethane, polyamide, polyacrylate, polysiloxane, polycarbonate, polysulfonamide, polymers of urea and formaldehyde, melamine and formaldehyde, melamine and urea, or melamine and glyoxal and mixtures thereof.

3. The microcapsule slurry according to claim 2, wherein the second material is polyurea and/or polyurethane.

4. The microcapsule slurry according to claim 1,
   wherein the coacervate comprises a first polyelectrolyte and a second polyelectrolyte, wherein the first polyelectrolyte is selected from the group consisting of proteins, polypeptides, polysaccharides or mixtures thereof, and wherein the second polyelectrolyte is selected from the group consisting of gum arabic, alginate salts, cellulose derivatives, guar gum, pectinate salts, carrageenan, polyacrylic and methacrylic acid, and xanthan gum.

5. The microcapsule slurry according to claim 1, wherein the oil phase core comprises a perfume oil.

6. A microcapsule powder obtained by drying the microcapsule slurry as defined in claim 1.

7. A consumer product comprising:
a consumer product base, and
the microcapsule slurry as defined in claim 1.

8. The consumer product according to claim 7, wherein the consumer product is in the form of a fabric softener composition comprising:
between 85 and 99.95% of the consumer product base comprising a fabric softener active base, by weight based on the total weight of the composition; and
between 0.05 to 15 wt %, by weight of the microcapsule slurry.

9. The consumer product according to claim 7, wherein the consumer product is in the form of a liquid detergent composition comprising:
between 85 and 99.95% of the consumer product base comprising a liquid detergent active base, by weight based on the total weight of the composition; and
between 0.05 to 15 wt %, by weight of the microcapsule slurry.

10. The consumer product according to claim 7, wherein the consumer product is in the form of a solid detergent composition comprising:
between 85 and 99.95% of the consumer product base comprising a solid detergent active base, by weight based on the total weight of the composition; and
between 0.05 to 15 wt %, by weight of the microcapsule slurry.

11. The consumer product according to claim 10, wherein the consumer product is in the form of a shampoo or a shower gel composition comprising:
between 85 and 99.95% of the consumer product base comprising a shampoo active base,
by weight based on the total weight of the composition; and
between 0.05 to 15 wt %, by weight of the microcapsule slurry.

12. The consumer product according to claim 7, wherein the consumer product is in the form of rinse-off conditioning composition comprising:
between 85 and 99.95% of the consumer product base comprising a rinse-off conditioner active base, by weight based on the total weight of the composition; and
between 0.1 to 15 wt %, by weight of the microcapsule slurry.

13. A consumer product comprising:
a consumer product base, and
a microcapsule powder as defined in claim 6.

14. The consumer product according to claim 8, wherein the fabric softener active base is selected from the group consisting of dialkyl quaternary ammonium salts, dialkyl ester quaternary ammonium salts, Hamburg esterquat, triethanolamine quat, silicones, and mixtures thereof.

15. The consumer product according to claim 9, wherein the liquid detergent active base is selected from the group consisting of an anionic surfactant, a nonionic surfactant, and mixtures thereof, wherein the anionic surfactant is selected from the group consisting of alkylbenzenesulfonate (ABS), secondary alkyl sulfonate (SAS), primary alcohol sulfate (PAS), lauryl ether sulfate (LES), and methyl ester sulfonate (MES), and wherein the nonionic surfactant is selected from the group consisting of alkyl amines, alkanolamide, fatty alcohol poly (ethylene glycol) ether, fatty alcohol ethoxylate (FAE), ethylene oxide (EO), propylene oxide (PO) copolymers, amine oxydes, alkyl polyglucosides, and alkyl polyglucosamides.

16. The consumer product according to claim 10, wherein the solid detergent active base is selected from the group consisting of an anionic surfactant, a nonionic surfactant, and mixtures thereof, wherein the anionic surfactant is selected from the group consisting of alkylbenzenesulfonate (ABS), secondary alkyl sulfonate (SAS), primary alcohol sulfate (PAS), lauryl ether sulfate (LES), and methyl ester sulfonate (MES), and wherein the nonionic surfactant is selected from the group consisting of alkyl amines, alkanolamide, fatty alcohol poly (ethylene glycol) ether, fatty alcohol ethoxylate (FAE), ethylene oxide (EO), propylene oxide (PO) copolymers, amine oxydes, alkyl polyglucosides, and alkyl polyglucosamides.

17. The consumer product according to claim 11, wherein the shampoo active base is selected from the group consisting of sodium alkylether sulfate, ammonium alkylether sulfates, alkylamphoacetate, cocamidopropyl betaine, cocamide MEA, alkylglucosides and aminoacid based surfactants.

* * * * *